(12) United States Patent
Kaneko et al.

(10) Patent No.: US 10,241,161 B2
(45) Date of Patent: Mar. 26, 2019

(54) MAGNETIC RESONANCE IMAGING DEVICE AND IMAGING PARAMETER DETERMINATION METHOD

(71) Applicant: Hitachi, Ltd., Tokyo (JP)

(72) Inventors: Yukio Kaneko, Tokyo (JP); Yoshihisa Soutome, Tokyo (JP); Hisaaki Ochi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 587 days.

(21) Appl. No.: 14/898,154

(22) PCT Filed: Jul. 23, 2014

(86) PCT No.: PCT/JP2014/069486
§ 371 (c)(1),
(2) Date: Dec. 14, 2015

(87) PCT Pub. No.: WO2015/029652
PCT Pub. Date: Mar. 5, 2015

(65) Prior Publication Data
US 2016/0146910 A1     May 26, 2016

(30) Foreign Application Priority Data
Aug. 27, 2013  (JP) .................................. 2013-175896

(51) Int. Cl.
*G01R 33/28* (2006.01)
*A61B 5/055* (2006.01)
(Continued)

(52) U.S. Cl.
CPC ............ *G01R 33/288* (2013.01); *A61B 5/055* (2013.01); *A61B 5/748* (2013.01);
(Continued)

(58) Field of Classification Search
CPC .............. G01R 33/288; G01R 33/3875; G01R 33/4833; A61B 5/055; A61B 5/748
See application file for complete search history.

(56) References Cited

U.S. PATENT DOCUMENTS

2007/0108976 A1   5/2007  Morich et al.
2009/0322329 A1   12/2009 Diehl et al.
(Continued)

FOREIGN PATENT DOCUMENTS

JP    2007-509686 A    4/2007
JP    2010-000358 A    1/2010
(Continued)

OTHER PUBLICATIONS

"Spatial domain method for the design of RF pulses in multicoil parallel excitation", W. Grissom, C. Y. Yip, Z. Zhang, V. A. Stenger, J. A. Fessler, and D. C. Noll, Magnetic Resonance in Medicine, 56, pp. 620-629 (2006).*

(Continued)

*Primary Examiner* — Daniel Miller
(74) *Attorney, Agent, or Firm* — Mattingly & Malur, PC

(57) ABSTRACT

Provided is a technique capable of achieving safety and image quality at the same time in an MRI device using a transmission coil including plural channels. An SAR distribution is calculated, and an imaging parameter is determined for optimizing a radio frequency magnetic field distribution in an imaging region while suppressing a maximum value of an SAR to be equal to or smaller than a predetermined threshold value. The determined imaging parameter includes a radio frequency magnetic field parameter for specifying radio frequency pulses to be transmitted through each of the plural channels. The SAR distribution is calculated using a (Continued)

database that retains an electric field distribution of each of the plural channels for each subject model retained in advance.

13 Claims, 15 Drawing Sheets

(51) Int. Cl.
    *G01R 33/483*     (2006.01)
    *A61B 5/00*     (2006.01)
    *G01R 33/3875*     (2006.01)
    *G01R 33/34*     (2006.01)
    *G01R 33/561*     (2006.01)

(52) U.S. Cl.
    CPC ..... *G01R 33/3875* (2013.01); *G01R 33/4833* (2013.01); *A61B 2560/0266* (2013.01); *G01R 33/34046* (2013.01); *G01R 33/4835* (2013.01); *G01R 33/5612* (2013.01)

(56) References Cited

U.S. PATENT DOCUMENTS

| | | |
|---|---|---|
| 2012/0013337 A1 | 1/2012 | Graesslin et al. |
| 2012/0019247 A1 | 1/2012 | Boernert et al. |
| 2012/0197106 A1* | 8/2012 | Cloos ................... G01R 33/246 600/411 |
| 2013/0063143 A1* | 3/2013 | Adalsteinsson .... G01R 33/5612 324/307 |

FOREIGN PATENT DOCUMENTS

| | | |
|---|---|---|
| JP | 2012-522562 A | 9/2012 |
| JP | 2012-522563 A | 9/2012 |

OTHER PUBLICATIONS

International Preliminary Report on Patentability received in corresponding International Application No. PCT/JP2014/069486 dated Mar. 10, 2016.

International Search Report of PCT/JP2014/069486.

Manuel Murbach et al., Local SAR enhancements in anatomically correct children and adult models as a function of position within 1.5 T MR body coil, Progress in Biophysics and Molecular Biology 107 (2011), pp. 428-433.

* cited by examiner

FIG.2
(A)
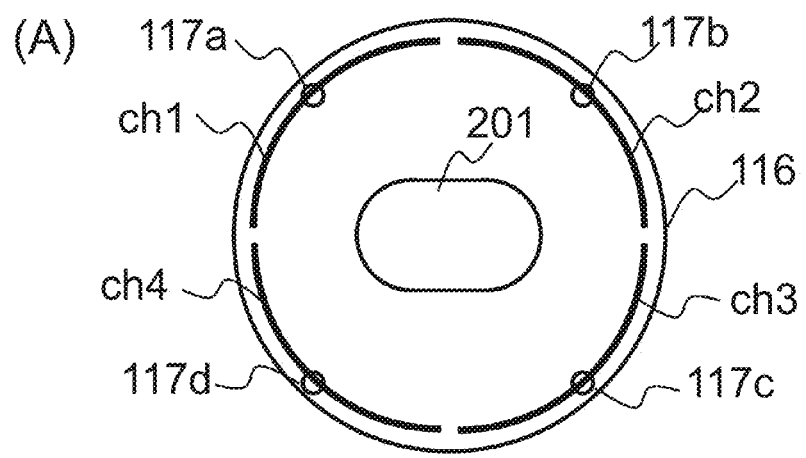
(B)
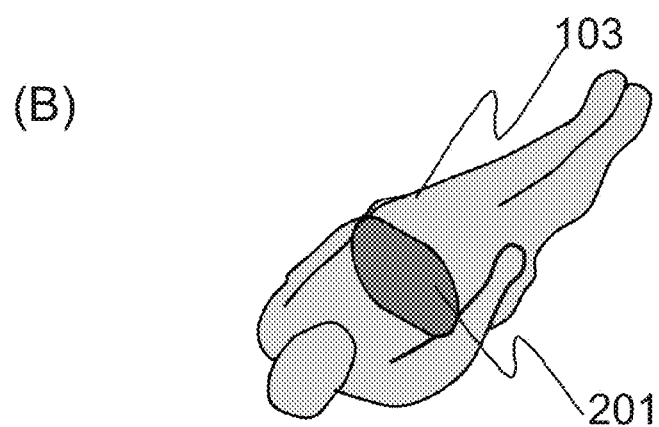
(C)
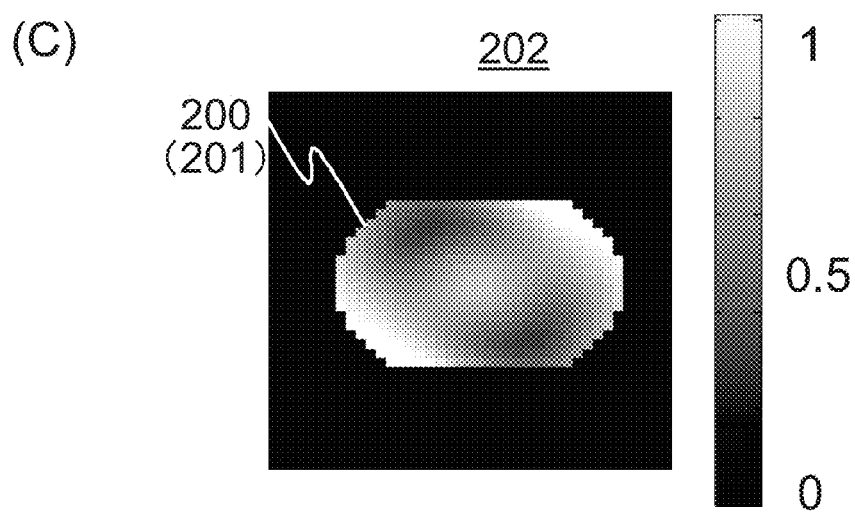

FIG.6

| HUMAN BODY MODEL | IMAGING PORTION | POSTURE | DENSITY ρ | CONDUCTIVITY σ | ELECTRIC FIELD DISTRIBUTION | | | |
|---|---|---|---|---|---|---|---|---|
| | | | | | Ch1 (E1) | Ch2 (E2) | Ch3 (E3) | Ch4 (E4) |
| | | | | | | | | |
| | | | | | | | | |

350

FIG.9
(A)
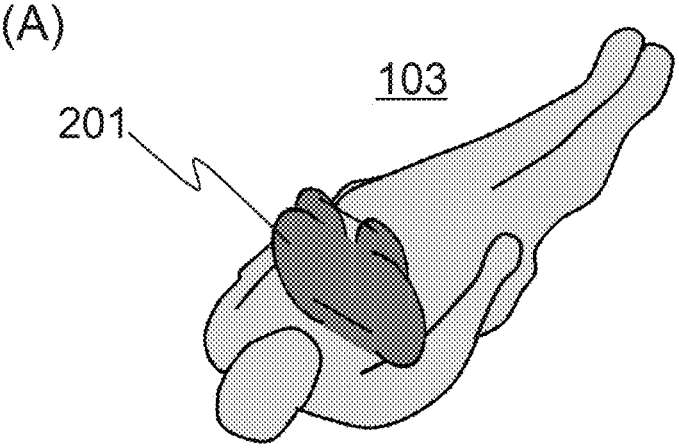
(B)
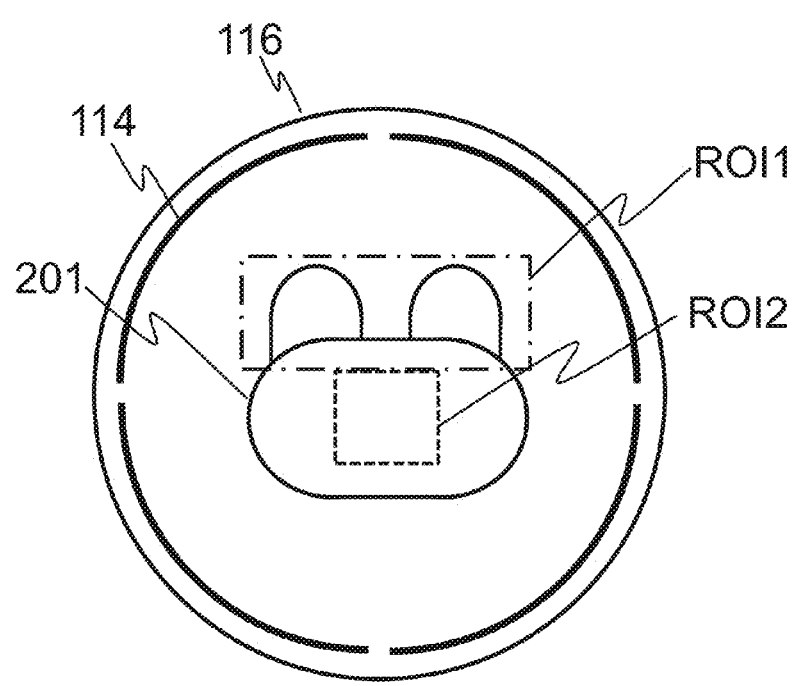

FIG.10
(A)
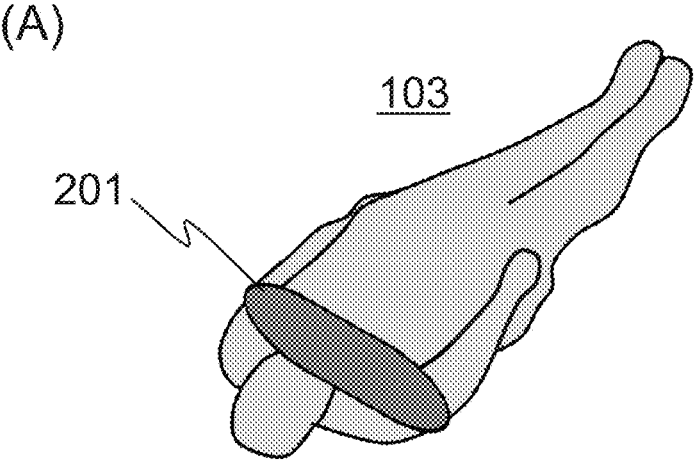
(B)
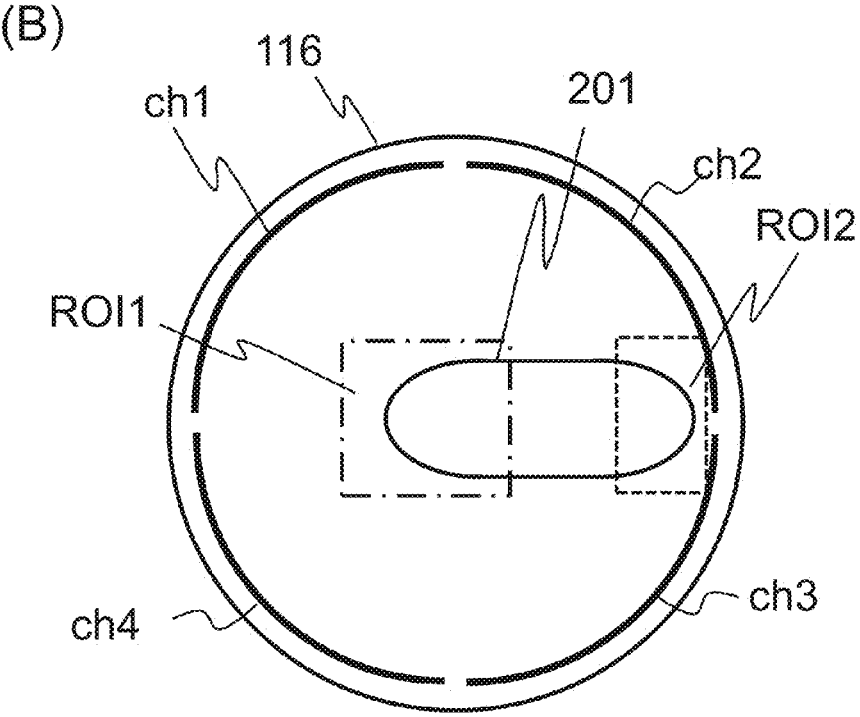

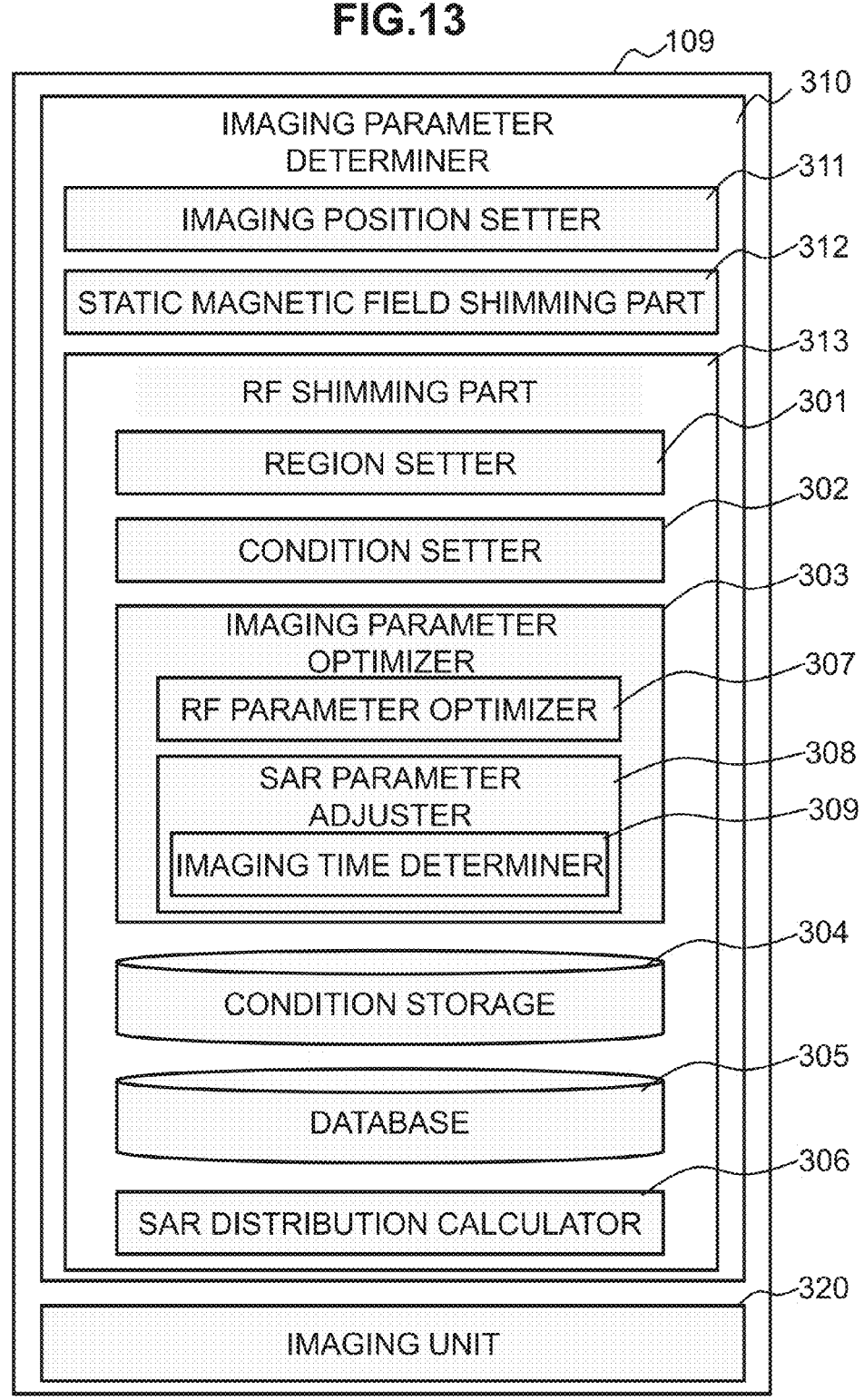

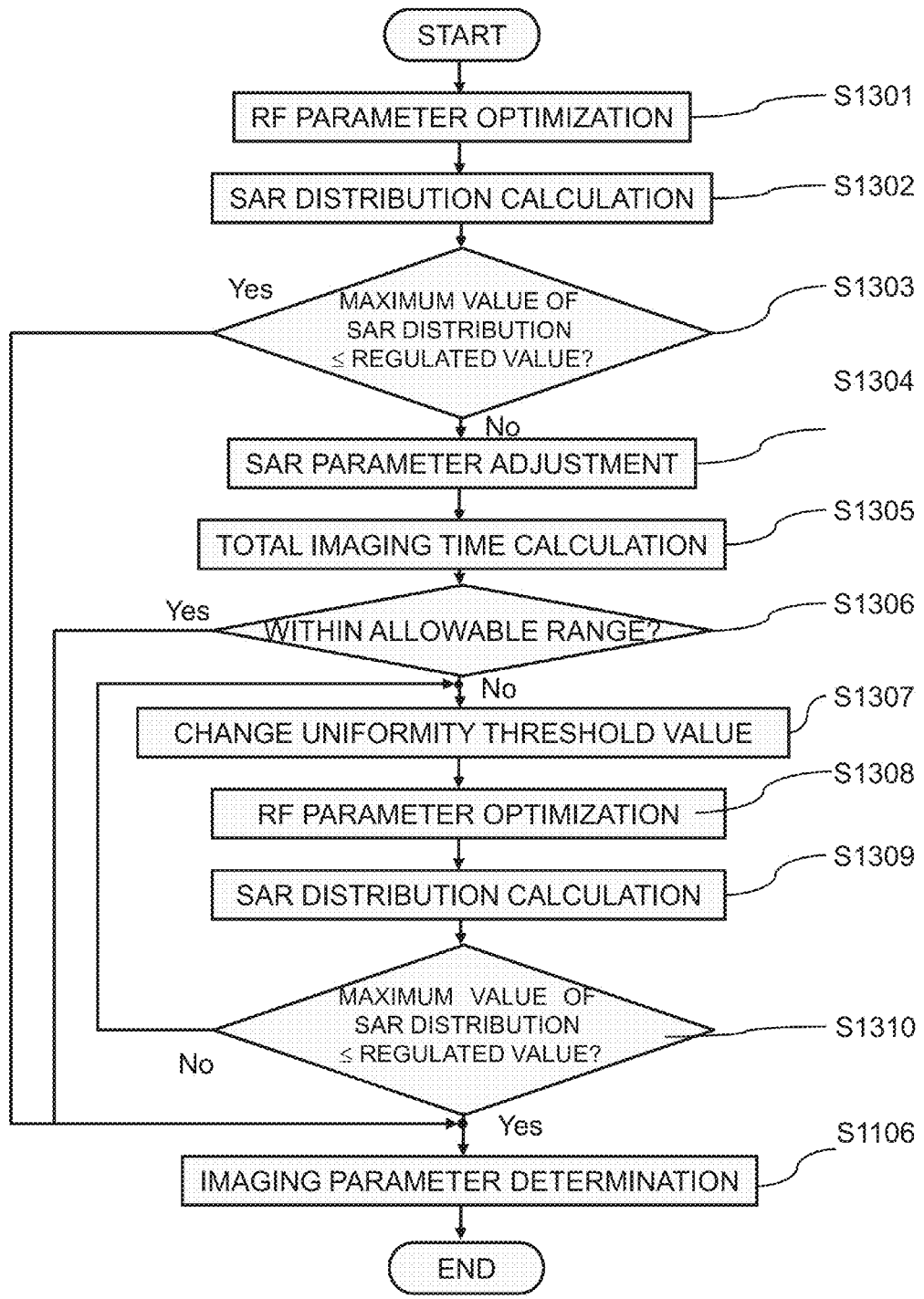

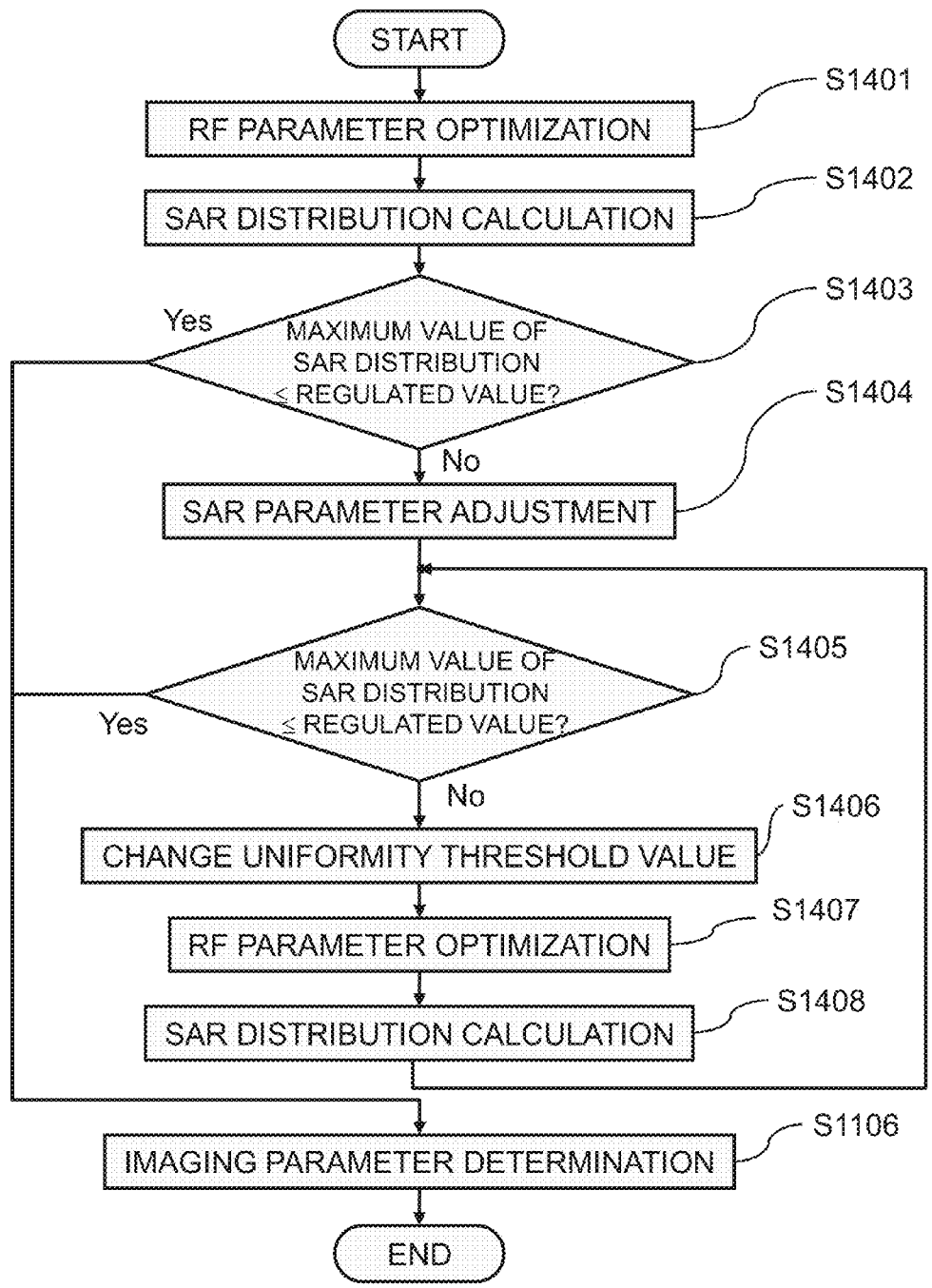

MAGNETIC RESONANCE IMAGING DEVICE AND IMAGING PARAMETER DETERMINATION METHOD

TECHNICAL FIELD

The present invention relates to a magnetic resonance imaging (MRI) technique, and more particularly, to a radio frequency magnetic field emission technique for generating a rotating magnetic field that induces a magnetic resonance phenomenon.

BACKGROUND ART

An MRI device is a medical image diagnosis device that generates magnetic resonance in an atomic nucleus in an arbitrary section that crosses a test object to obtain a tomographical image in the section from a generated magnetic resonance signal. The MRI device transmits a radio frequency wave (hereinafter, referred to as RF) which is a type of electromagnetic wave to the test object, excites spin of the atomic nucleus in the test object, receives a nuclear magnetic resonance signal generated by the nuclear-spin, and images the test object. The transmission of the RF to the test object is performed by an RF transmission coil, and the reception of the nuclear magnetic resonance signal from the test object is performed by an RF reception coil.

In recent years, in order to enhance a signal-to-noise ratio (SNR) of an image, a static magnetic field intensity may tend to increase, and a high magnetic field MRI device (super-high magnetic field MRI device) in which a static magnetic field intensity tends to be strong to be 3 T (teslas) or higher has been spread. However, as the static magnetic field intensity increases, the SNR is enhanced, but unevenness in a captured image easily occurs. This is because the frequency of an RF used for induction of the magnetic resonance phenomenon increases according to the increase in the magnetic field. For example, in an MRI device having a static magnetic field intensity of 3 T (teslas) (hereinafter, referred to as a 3 T MRI device), an RF having a frequency of 128 MHz is used. In a living body, a wavelength of such an RF is about 30 cm which is approximately the same size as that of an abdomen section, and a change occurs in its phase. An emitted RF distribution and a space distribution of a rotating magnetic field that induces the magnetic resonance phenomenon (hereinafter, referred to as a radio frequency magnetic field distribution $B_1$) that is generated by the RF become non-uniform by change in the phase, which makes image unevenness. Accordingly, in RF emission performed in an ultra-high magnetic field MRI device, a technique for reducing non-uniformity of distribution of the rotating magnetic field $B_1$ is necessary.

As an RF emission method for reducing the non-uniformity of the $B_1$ distribution, a method called "RF shimming" is used. This is a method for controlling, using a transmission coil having plural channels, controlling a phase and an amplitude of RF pulses given to each channel to reduce the $B_1$ non-uniformity in an imaging region. The $B_1$ distribution of each channel is measured in advance before main imaging, and an amplitude and a phase of optimal RF pulses for reducing the $B_1$ non-uniformity are calculated using the $B_1$ distribution. Here, a region to be diagnosed which is a partial region in a section is set as a region of interest (ROI), and the amplitude and the phase are determined so that the $B_1$ non-uniformity in the ROI is reduced.

Further, in the MRI device, a specific absorption rate (SAR) of the RF in the living body is regulated to be in a predetermined range in consideration of safety for the living body. A technique for setting RF pulses so that an SAR in the whole living body (hereinafter, a whole body SAR) becomes as small as possible in consideration of the regulation is proposed (for example, see PTL 1). However, in addition to the whole body SAR, an SAR locally generated in the living body (hereinafter, referred to as a local SAR) may also be considered. The whole body SAR may be measured with accuracy to some extent, but it is difficult to measure the local SAR. Accordingly, the local SAR is calculated by data analysis using a numerical simulation, or the like (for example, see NPL 1). Further, as a method for controlling the local SAR, when repeating RF pulses in a multi-shot sequence, a technique for changing a region where energy concentrates, that is, a position of an SAR hot spot by changing each pulse waveform has been proposed (for example, see PTL 2).

CITATION LIST

Patent Literature

PTL 1: JP-T-2012-522563
PTL 2: JP-T-2012-522562

Non-Patent Literature

NPL 1: Manuel M. et al., Local SAR enhancements in anatomically correct children and adult models as a function of position within 1.5 T MR body coil, Progress in Biophysics and Molecular Biology, NMR in Biomedicine, 2011, pp. 428-433

SUMMARY OF INVENTION

In such an MRI device, according to increase in the magnetic field, an artifact generated by a body motion or the like noticeably increases, and the frequency of an RF to be used becomes high, and thus, the SAR also increases.

In the technique disclosed in PTL 1, the whole body SAR is reduced, but the local SAR is not controlled. Further, in the technique disclosed in NPL 1, a local SAR distribution in a human body model is calculated using the numerical simulation and human body models having various shapes, but a method for controlling the local SAR is not disclosed. Further, the technique disclosed in PTL 2 is premised on the multi-shot sequence, and cannot be applied to all types of sequences. In addition, in a multi-shot MR sequence as in the technique disclosed in PTL 2, in order to change waveforms of individual RF pulses, a complicated process in software is necessary. In this way, in the related art, there is no technique for controlling the local SAR while suppressing the non-uniformity of the high frequency magnetic field. That is, it is difficult to achieve safety and enhancement of image quality in a region of interest at the same time.

Considering the above-mentioned problems, the invention aims to provide a technique capable of achieving safety and image quality regardless of an imaging sequence, in an MRI device that uses a transmission coil including plural channels.

According to an aspect of the invention, there is provided a technique of calculating an SAR distribution and determining an imaging parameter for optimizing a radio frequency magnetic field distribution in an imaging region while suppressing a maximum value of an SAR to be equal to or smaller than a predetermined threshold value. The determined imaging parameter includes a radio frequency magnetic field parameter for specifying radio frequency pulses to be transmitted through each of plural channels. The SAR distribution is calculated using a database that retains an electric field distribution of each of the plural channels for each subject model retained in advance.

According to the invention, in an MRI device that uses a transmission coil including plural channels, it is possible to safely obtain a high quality image regardless of an imaging sequence.

BRIEF DESCRIPTION OF DRAWINGS

FIG. 2(A) is a diagram illustrating a transmission coil of the first embodiment, FIG. 2(B) is a diagram illustrating an imaging region of the first embodiment, and FIG. 2(C) is a diagram illustrating a simulation result of a distribution of a rotating magnetic field $B_1$ generated in a phantom of the first embodiment.

FIG. 6 is a diagram illustrating an example of data retained in the database of the first embodiment.

FIG. 9(A) is a diagram illustrating an imaging region in imaging the breast in the first embodiment, and FIG. 9(B) is a diagram illustrating a setting example of a first region and a second region in imaging the breast in the first embodiment.

FIG. 10(A) is a diagram illustrating an imaging region in imaging the shoulder in the first embodiment, and FIG. 10(B) is a diagram illustrating a setting example of a first region and a second region in imaging the shoulder in the first embodiment.

FIG. 13 is a functional block diagram illustrating a computer of a third embodiment.

FIG. 14 is a flowchart illustrating an imaging parameter optimization process of the third embodiment.

FIG. 15 is a flowchart illustrating a modification example of the imaging parameter optimization process of the third embodiment.

DESCRIPTION OF EMBODIMENTS

Hereinafter, embodiments of the invention will be described with reference to the accompanying drawings. In all the drawings for describing the respective embodiments, the same reference signs are given to components having the same functions, and repetitive description thereof will be omitted. The respective embodiments do not limit the invention.

First Embodiment

Figure 1:
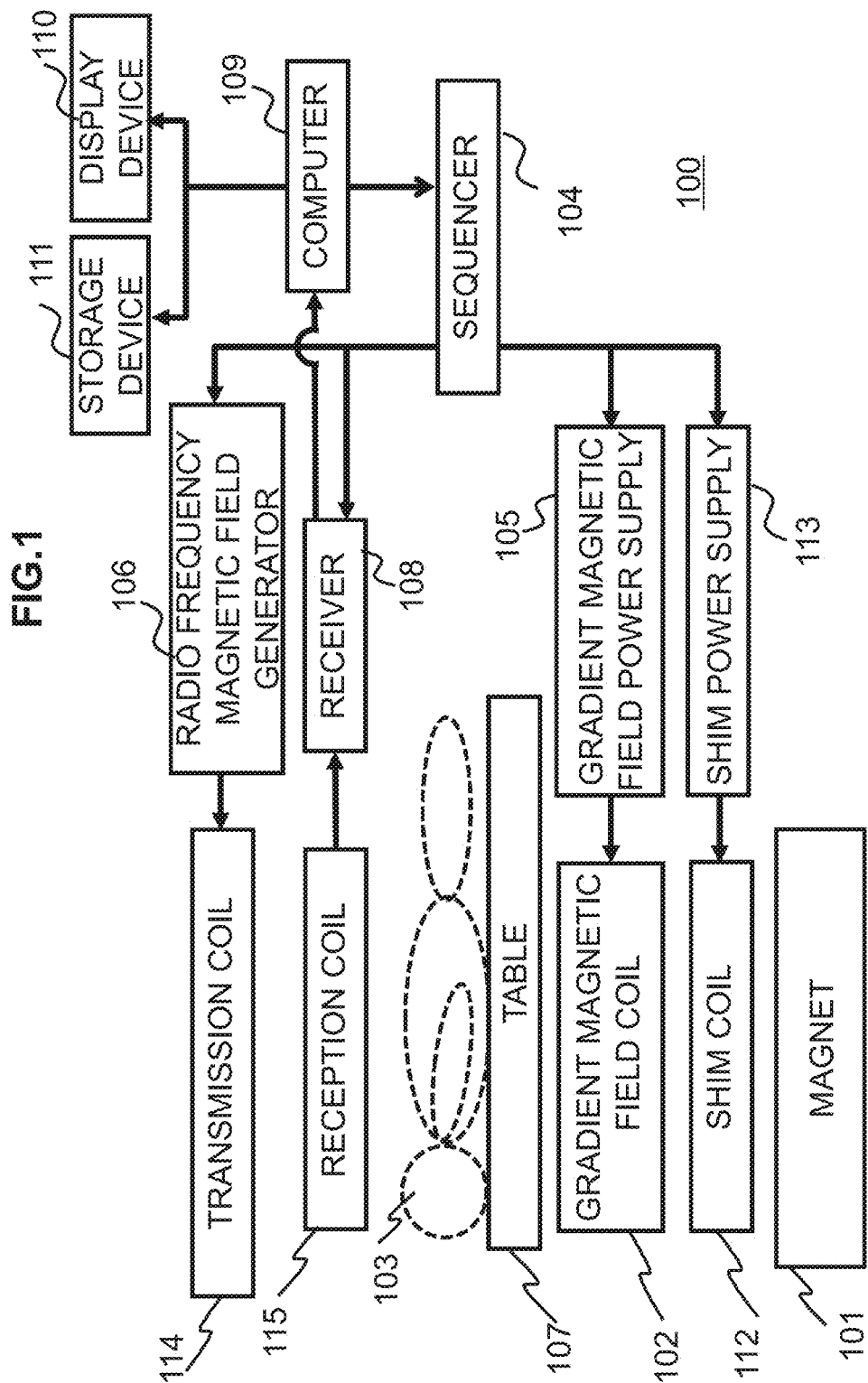
FIG. 1 is a block diagram illustrating an MRI device of a first embodiment.

A first embodiment of the invention will be described. First, an overall configuration of an MRI device of this embodiment will be described. FIG. 1 is a block diagram illustrating an MRI device 100 of this embodiment. As shown in FIG. 1, the MRI device 100 of this embodiment includes a magnet 101 that generates a static magnetic field, a coil 102 (gradient magnetic field coil) that generates a gradient magnetic field, a shim coil 112 that adjusts static magnetic field uniformity, a sequencer 104, an RF transmission coil (transmission coil) 114 that emits (transmits) a radio frequency magnetic field, an RF reception coil (reception coil) 115 that detects (receives) a nuclear magnetic resonance signal generated from a subject 103, a table 107 on which the subject 103 is mounted, a gradient magnetic field power supply 105, a radio frequency magnetic field generator 106, a receiver 108, a shim power supply 113, and a computer 109 that controls the respective components of the MRI device 100 and realizes imaging.

The gradient magnetic field coil 102 and the shim coil 112 are connected to the gradient magnetic field power supply 105 and the shim power supply 113, respectively. Further, the transmission coil 114 and the reception coil 115 are connected to the radio frequency magnetic field generator 106 and the receiver 108, respectively.

The sequencer 104 transmits a command to the gradient magnetic field power supply 105 and the shim power supply 113, and the radio frequency magnetic field generator 106 according to an instruction from the computer 109 to respectively generate a gradient magnetic field and a radio frequency magnetic field (RF). The RF is applied (transmitted) to the subject 103 through the transmission coil 114. A nuclear magnetic resonance signal generated from the subject 103 as the RF is applied (transmitted) thereto is detected (received) by the reception coil 115, and is detected by the receiver 108. A nuclear magnetic resonance frequency that serves as a detection reference in the receiver 108 is set through the sequencer 104 by the computer 109. The detected signal is transmitted to the computer 109 through an A/D conversion circuit, and is subjected to signal processing such as image reconstruction. The result is displayed on a display device 110 connected to the computer 109. The detected signal or a measurement condition is stored in a storage device 111 connected to the computer 109, as necessary.

The magnet 101, the shim coil 112, and the shim power supply 113 form a static magnetic field forming unit that forms a static magnetic field space. The gradient magnetic field coil 102 and the gradient magnetic field power supply 105 form a gradient magnetic field application unit that applies a gradient magnetic field in the static magnetic field space. Further, the transmission coil 114 and the radio frequency magnetic field generator 106 form a radio frequency magnetic field transmission unit that emits (transmits) an RF to the subject 103. The reception coil 115 and the receiver 108 form a signal reception unit that detects (receives) a nuclear magnetic resonance signal generated from the subject 103.

The transmission coil 114 of this embodiment is configured by a multi-channel coil that includes plural channels that transmit independent RF pulses respectively. FIG. 2(A) shows an example of the transmission coil 114 of this embodiment. Here, an example in which the transmission coil 114 is a four-channel (4 ch) coil that includes four channels (ch1, ch2, ch3, and ch4) is shown. Amplitudes and phases of RF pulses transmitted through the respective channels (ch1, ch2, ch3, and ch4) are independently set by the computer 109, respectively. The radio frequency magnetic field generator 106 of this embodiment independently transmits RF waveforms to the respective channels (ch1, ch2, ch3, and ch4) through power supply points (117a, 117b, 117c, and 117d) provided in the respective channels, under the control of the computer 109. In the figure, reference numeral 116 represents an RF shield.

The computer 109 of this embodiment optimizes a $B_1$ distribution in a region of interest ROI while appropriately controlling a local SAR, and controls respective components relating to imaging of the MRI device 100 to safely obtain an image in which the region of interest ROI shows a high image quality. Here, a whole body SAR or an artifact is also appropriately suppressed, to thereby achieve higher stability and quality.

Figure 3:
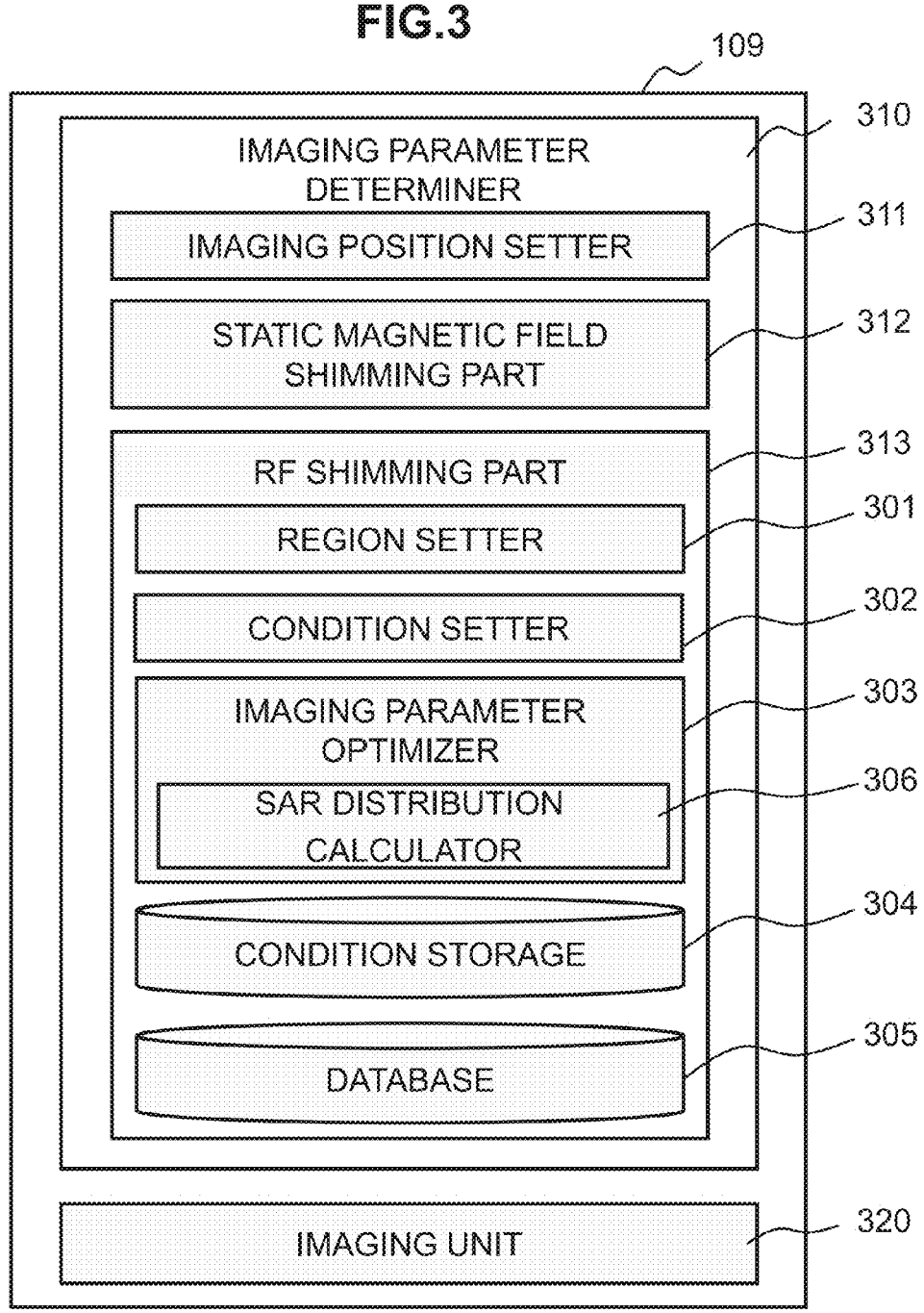
FIG. 3 is a functional block diagram of a computer of the first embodiment.

In order to realize the above performance, as shown in FIG. 3, the computer 109 of this embodiment includes an imaging parameter determiner 310 that determines a predetermined imaging parameter among imaging conditions set by a user, and an imaging unit 320 that performs main imaging using the imaging parameter set by the imaging parameter determiner 310. Further, the imaging parameter determiner 310 includes an imaging position setter 311, a static magnetic field shimming part 312, an RF shimming part 313.

The imaging position setter 311 sets an imaging position (imaging section). The imaging section is set using a positioning image obtained by executing scout scanning or the like before performing the main imaging. For example, a designation from a user is received on the positioning image displayed in the display device 110, and the designated position is set as the imaging section. As the imaging section, a predetermined position may be automatically set by using a feature point or the like on the positioning image as a clue. A region of the subject 103 on the imaging section is referred to as an imaging region.

The static magnetic field shimming part 312 measures a static magnetic field distribution, and performs adjustment so that a static magnetic field becomes as uniform as possible. The adjustment is performed by operating the shim coil 112 through the shim power supply 113. When the adjustment of the uniformity of the static magnetic field is not necessary, the static magnetic field shimming part 312, the shim power supply 113, and the shim coil 112 may not be provided.

The RF shimming part 313 performs an RF shimming process of optimizing the $B_1$ distribution in the imaging region. In this embodiment, the RF shimming part 313 determines a parameter (hereinafter, referred to as an RF parameter) for specifying RF pulses transmitted through each of channels (ch1, ch2, ch3, and ch4) of the transmission coil 114 so that the $B_1$ distribution is optimized. In this embodiment, it is assumed that the RF parameter is at least one of the amplitude and phase of the RF pulses.

Further, in this embodiment, in the RF shimming process, the RF shimming part 313 determines the RF parameter capable of increasing the uniformity of the $B_1$ distribution in the region of interest ROI while appropriately controlling a local SAR and suppressing at least one of a whole body SAR and an artifact. Thus, it is possible to safely and efficiently obtain an image in which the region of interest ROI shows a high image quality.

In order to realize the above performance, the RF shimming part 313 of this embodiment includes a region setter 301, a condition setter 302, an imaging parameter optimizer 303, a condition storage 304, and a database 305. Further, the imaging parameter optimizer 303 includes an SAR distribution calculator 306.

Before describing configurations of respective components that realize the RF shimming process of this embodiment by the RF shimming part 313, an RF emission method using the transmission coil 114 of this embodiment will be briefly described. Here, an example in which an abdominal region of the subject 103 is imaged will be described as an example. When imaging the abdominal region, as shown in FIG. 2(B), an imaging region 201 is set.

When an RF is applied to a phantom 200 obtained by resembling the abdominal region of the subject 103 from the transmission coil 114, an electromagnetic field simulation result of a rotating magnetic field $B_1$ ($B_1$ distribution) 202 generated in the imaging region 201 in the phantom 200 is shown in FIG. 2(C).

In this simulation, a $B_1$ intensity in the imaging region 201 is set to be non-dimensional so that a maximum $B_1$ intensity in the phantom 200 becomes 1. The sizes of the phantom 200 in x-, y-, and z-axial directions are set to 300 mm, 200 mm, and 900 mm, respectively. These sizes correspond to a shape obtained by assuming and simplifying an abdominal section of a living body. Further, physical properties of the phantom 200 are set to have a conductivity of 0.6 S/m and a dielectric constant of 80. These properties are determined in consideration of a water phantom close to physical properties of a living body. The frequency of the applied RF is set to 128 MHz in consideration of an MRI device of 3 T.

Further, sine-waveform voltages (B_ch1, B_ch2, B_ch3, and B_ch4) shown in the following Expression (1) are supplied to power supply points (117a, 117b, 117c, and 117d) of the respective channels (ch1, ch2, ch3, and ch4).

[Expression 1]

$$\left.\begin{aligned} B\_ch1 &= A1\sin(\omega t + \phi 1) \\ B\_ch2 &= A2\sin(\omega t + \phi 2) \\ B\_ch3 &= A3\sin(\omega t + \phi 3) \\ B\_ch4 &= A4\sin(\omega t + \phi 4) \end{aligned}\right\} \quad (1)$$

Here, A1 and $\phi 1$ represent an amplitude and a phase of a sine-waveform voltage supplied to the power supply point 117a of the channel ch1, A2 and $\phi 2$ represent an amplitude and a phase of a sine-waveform voltage supplied to the power supply point 117b of the channel ch2, A3 and $\phi 3$ represent an amplitude and a phase of a sine-waveform voltage supplied to the power supply point 117c of the channel ch3, and A4 and $\phi 4$ represent an amplitude and a phase of a sine-waveform voltage supplied to the power supply point 117d of the channel ch4. Further, the $B_1$ distribution 202 shown in FIG. 2(C) shows a distribution when A1, A2, A3 and A4 are all set to 1 and phases are set such that $\phi 1=0$, $\phi 2=\pi/2$, $\phi 3=\pi$, and $\phi 4=3\pi/2$. This is an RF emission method called as quadrature driving (QD), which is a standard RF emission method.

As in the QD emission, when an RF waveform is transmitted at different phases by $\pi/2$ at the same amplitude through the respective channels (ch1, ch2, ch3, and ch4), as shown in FIG. 2(C), in the imaging region 201 of the phantom 200, the $B_1$ intensity greatly varies to become non-uniform. This is $B_1$ non-uniformity which is a current problem in a high magnetic field MRI device.

The RF shimming part 313 of this embodiment adjusts, when a specific region to be diagnosed in the imaging region 201 is the region of interest ROI, amplitudes (A1, A2, A3, and A4) and phases (φ1, φ2, φ3, and φ4) of an RF transmitted to the respective channels (ch1, ch2, ch3, and ch4) so that the $B_1$ non-uniformity in the region of interest ROI is reduced, and sets optimal values as RF parameters. Here, the RF shimming part 313 of this embodiment optimizes the parameters while appropriately controlling a local SAR and suppressing at least one of a whole body SAR and an artifact.

The RF shimming part 313 of this embodiment first specifies the region of interest ROI where an image of a high image quality is to be acquired from an imaging region. Further, the RF shimming part 313 specifies a suppression region which is a region where an artifact is generated in the region of interest ROI. The suppression region is a region different from the region of interest. Further, the RF shimming part 313 determines the RF parameters so that at least one of a whole body SAR and an artifact is suppressed while increasing the $B_1$ uniformity in the region of interest ROI and appropriately controlling a local SAR.

Figure 4:
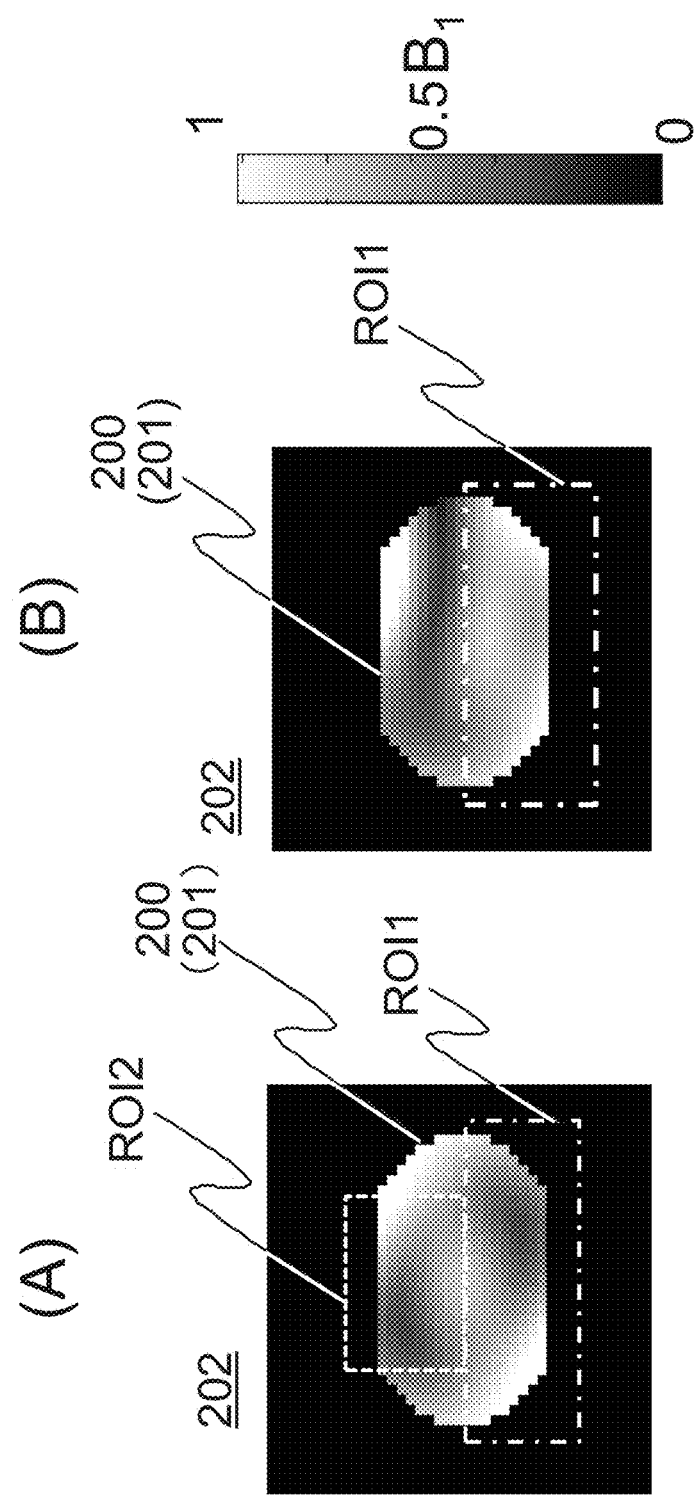
FIG. 4(A) is a diagram illustrating a setting example of a first region and a second region of the first embodiment.
FIG. 4(B) is a diagram illustrating a setting example of the first region of the first embodiment.

The region setter 301 sets the region of interest ROI and the suppression region as a first region ROI1 and a second region ROI2, respectively. The setting is respectively performed by receiving a region designated on a positioning image by a user, or on a result of $B_1$ distribution measurement performed using the RF parameters as initial values. That is, the region setter 301 sets the first region ROI1 and the second region ROI2 according to an instruction from the user. FIG. 4(A) shows a setting example of the first region ROI1 and the second region ROI2 when the abdomen is designated as an imaging portion.

As a region where an artifact is generated, for example, a region having a periodic physical motion, such as a fat region or a heart region, is set. The fat region has a large signal intensity from fat compared with other tissues, and thus, greatly contributes to the artifact regardless of whether its motion is periodic or random.

The first region ROI1 which is the region of interest and the second region ROI2 which is the suppression region may be configured to be automatically set according to an imaging portion and an imaging purpose. In this case, the MRI device 100 further includes a region storage that stores the first region ROI1 and the second region ROI2 in association with the portion and the imaging purpose. When the portion and the imaging purpose are set as imaging conditions, the region setter 301 extracts and sets the first region ROI1 and the second region ROI2 stored in association with the imaging portion or the imaging purpose set as the imaging conditions from the region storage. The region storage is registered in the storage device 111 in advance.

Further, when there is no region where an artifact is not generated in the first region ROI1, or if any, when the generated artifact is ignorable, as shown in FIG. 4(B), the second region ROI2 may not be selected.

The imaging parameter optimizer 303 determines at least one of the amplitudes (A1, A2, A3, and A4) and the phases (φ1, φ2, φ3, and φ4) of the RF transmitted to the respective channels (ch1, ch2, ch3, and ch4) as the RF parameters so that the $B_1$ distribution in the first region ROI1 is optimized while appropriately suppressing a local SAR. In this embodiment, under the condition that the maximum value of the local SAR does not exceed a predetermined regulated value, the optimization of the $B_1$ distribution in the first region ROI1 is realized by setting the uniformity of the $B_1$ distribution in the first region ROI1 to a predetermined value or greater, and by reducing at least one of a whole body SAR and an artifact.

In this embodiment, the RF parameters are obtained as a solution for minimizing a predetermined objective function under a predetermined restriction condition.

Calculation of the solution is performed using an optimization problem solution, for example, a steepest descent method, a gradient method, a Newton's method, a least-square method, a conjugate gradient method, a linear programming method, a non-linear programming method, a method for calculating an optimal solution by comprehensively changing values of amplitudes and phases, or the like.

Further, the solution for minimizing the objective function may be obtained by comprehensively changing the values of the amplitudes and the phases. For example, a value of the objective function is calculated while changing the values of the amplitude and the phase by 1 dB and a degree of 5°, and an amplitude and a phase where the value of the objective function is the minimum are obtained. Here, when it takes a massive calculation time when the amplitudes and the phases are comprehensively changed, for example, variations of the amplitude and the phase may be initially set to be large to obtain an amplitude and a phase where the minimum value of the objective function is obtained, and then, the variations may be set to be small in the vicinity of values of the obtained amplitude and phase to calculate the amplitudes and the phases. When performing the solution methods, initial values of the amplitude and the phase are retained in the storage device 111 in advance. Further, when optimal amplitude and phase are predicted in advance to a certain degree, the amplitudes and the phases may be comprehensively changed, using the predicted values as initial values, only with respect to values in the vicinity of the initial values.

Here, the imaging parameter optimizer 303 may perform $B_1$ distribution measurement for measuring the $B_1$ distribution in the imaging region whenever the RF parameters are changed to obtain a $B_1$ value in the imaging region. Further, only one of the amplitude and the phase may be changed to determine the RF parameters.

The condition storage 304 stores a set of a restriction condition and an objective function (optimization conditions) used in calculation of the RF parameters in the imaging parameter optimizer 303. The condition setter 302 extracts and sets optimization conditions used in calculation of the RF parameters in the imaging parameter optimizer 303 from the condition storage 304 according to an instruction of the user. The imaging parameter optimizer 303 calculates the RF parameters using the set optimization conditions.

The optimization conditions are stored in the condition storage 304 in association with at least one of an imaging portion and an imaging purpose, and the condition setter 302 may extract the optimization conditions from the condition storage 304 according to the imaging portion set by the user so that the optimization conditions can be automatically selected and set.

In this embodiment, the local SAR is defined as an SAR value in a desired (local) region in an SAR distribution in an imaging region. The SAR distribution calculator 306 of this embodiment calculates the SAR distribution using imaging conditions including the RF parameters.

The SAR distribution ($SAR_{dis}$) is represented by the following Expression (2) using a density ρ and a conductivity σ of a subject which is an imaging object, an electric field distribution of each channel, RF parameters (amplitude and phase) of each channel, the number n of applied RF pulses per unit time, and the number m of slices.

[Expression 2]

$$SAR_{dis} = \frac{\sigma}{\rho}\{(E1 \cdot A1 \cdot e^{i\phi 1})^2 + (E2 \cdot A2 \cdot e^{i\phi 2})^2 + (E3 \cdot A3 \cdot e^{i\phi 3})^2 + (E4 \cdot A4 \cdot e^{i\phi 4})^2\} \times n \times m \quad (2)$$

Here, E1, E2, E3, and E4 represent electric fields of the channels (ch1, ch2, ch3, and ch4), respectively, and A1, A2, A3, and A4 represent amplitudes of the channels (ch1, ch2, ch3, and ch4), respectively. Further, φ1, φ2, φ3, and φ4 represent phases of the channels (ch1, ch2, ch3, and ch4), respectively.

The density ρ and the conductivity σ of the subject which is the imaging object, and the electric field distribution of each channel are acquired from the database 305. Further, the number n of applied RF pulses per unit time, and the number m of slices are determined by imaging conditions. For example, the number n of applied RF pulses is determined by a TR (repetition time) of imaging parameters and a pulse sequence.

Figure 5:
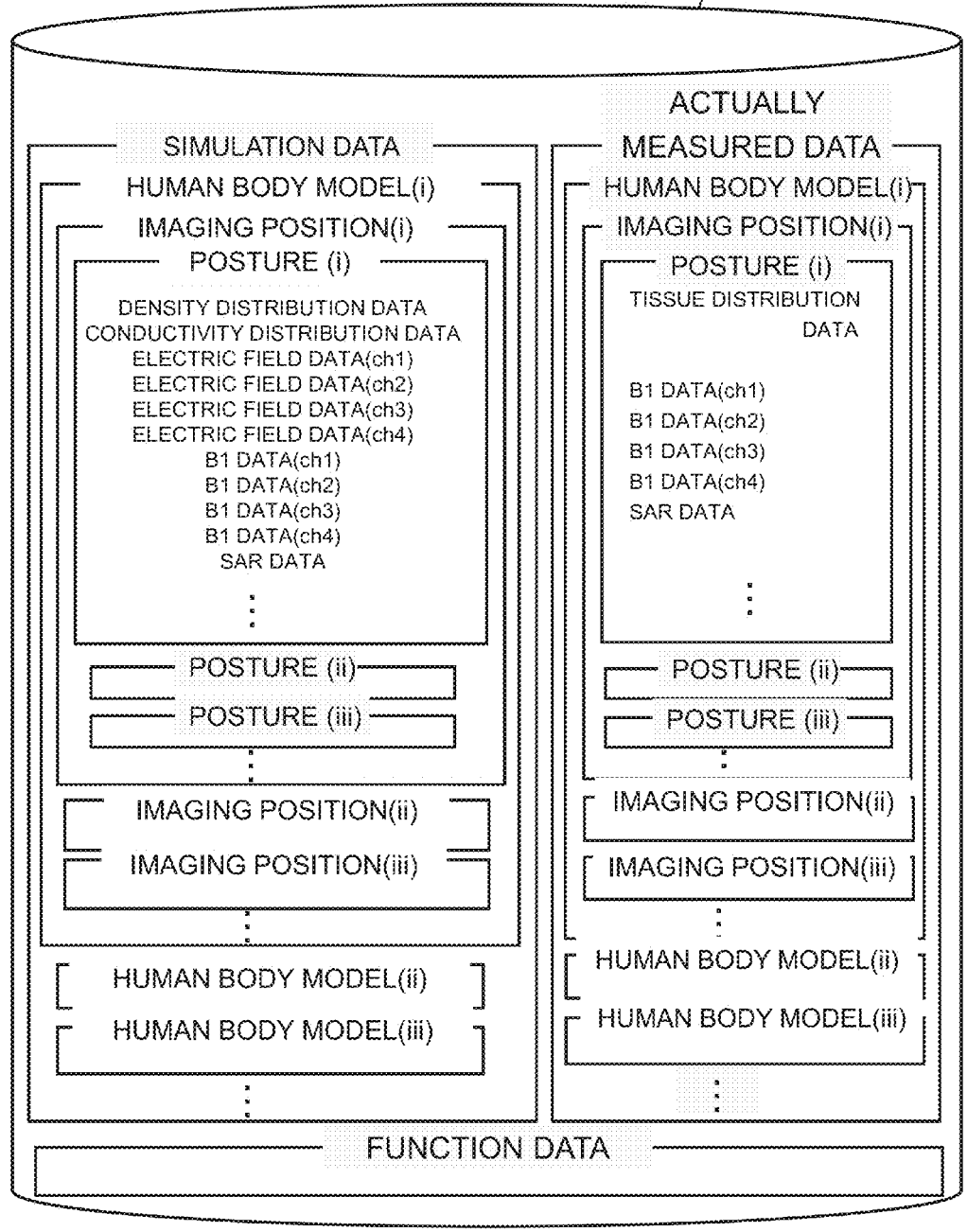
FIG. 5 is a diagram illustrating a database of the first embodiment.

The database 305 retains densities ρ and conductivities σ, electric field distribution data for the respective channels (ch1, ch2, ch3, and ch4), and the like in association with various human body models. FIG. 5 shows an image of the database 305.

As shown in the figure, the database 305 retains each set of data obtained by a simulation for each human body model, and/or each set of data obtained by actual measurement.

FIG. 6 shows an example of data 350 retained in the database 305. As shown in the figure, each set of data 350 is configured so that a density distribution ρ, a conductivity distribution σ, and an electric field distribution (E1, E2, E3, and E4) for each channel are associated with each human body model specified by its weight and height, each imaging portion, and each posture, for example.

For example, with respect to the size and weight that form the human body model, various sizes ranging from an infant to an adult are comprehensively accumulated. With respect to the adult, for example, a variety of human body model data ranging from a body form of a thin person to a body form of a fat person is accumulated. With respect to the imaging portion, for example, a head portion, a neck portion, a shoulder portion, a chest portion, a kidney portion, a stomach portion, a lumbar portion, a prostate portion, a knee portion, a heel portion, and the like are accumulated. With respect to the posture, for example, the position of an arm, bending of the knees, and the like are accumulated.

Further, the density ρ and the conductivity σ are physical properties specified for each type of tissue (fat, muscle, bone or the like).

As the electric field distribution for each channel, a value thereof when an RF magnetic field is emitted through each channel once per unit time at a phase and an amplitude (referred to as a reference phase and a reference amplitude, respectively) which is a reference when imaging one slice in the above-described various human body models, imaging portions and postures. Hereinafter, in this embodiment, it is assumed that the reference phase is 0 degree, and the reference amplitude is 1.

The SAR distribution calculator 306 of this embodiment calculates, based on subject information, an imaging portion, and a posture set as imaging conditions, an SAR distribution using data retained in the database 305 in association with a human body model, an imaging portion and a posture which are closest to information about the subject information, the imaging portion, and the posture set as the imaging conditions.

Further, data obtained by calculating a local specific absorption rate is retained in the database 305 in advance for each human body model, each imaging portion, and each posture, with respect to some representative RF emission methods (for example, QD emission which is emission with excellent uniformity and is method for minimizing an SAR, or the like). Further, a function that uses subject information, an imaging portion and a posture as variables and uses the local specific absorption rate as an output is created based on the data, and is retained in the database 305. The heights, weights or the like of the human body models are discrete values, but it is possible to calculate a local specific absorption rate with respect to an arbitrary height or weight using the function data. Thus, it is possible to simply calculate the local specific absorption rate at high speed and to determine the safety at high speed.

Figure 7:
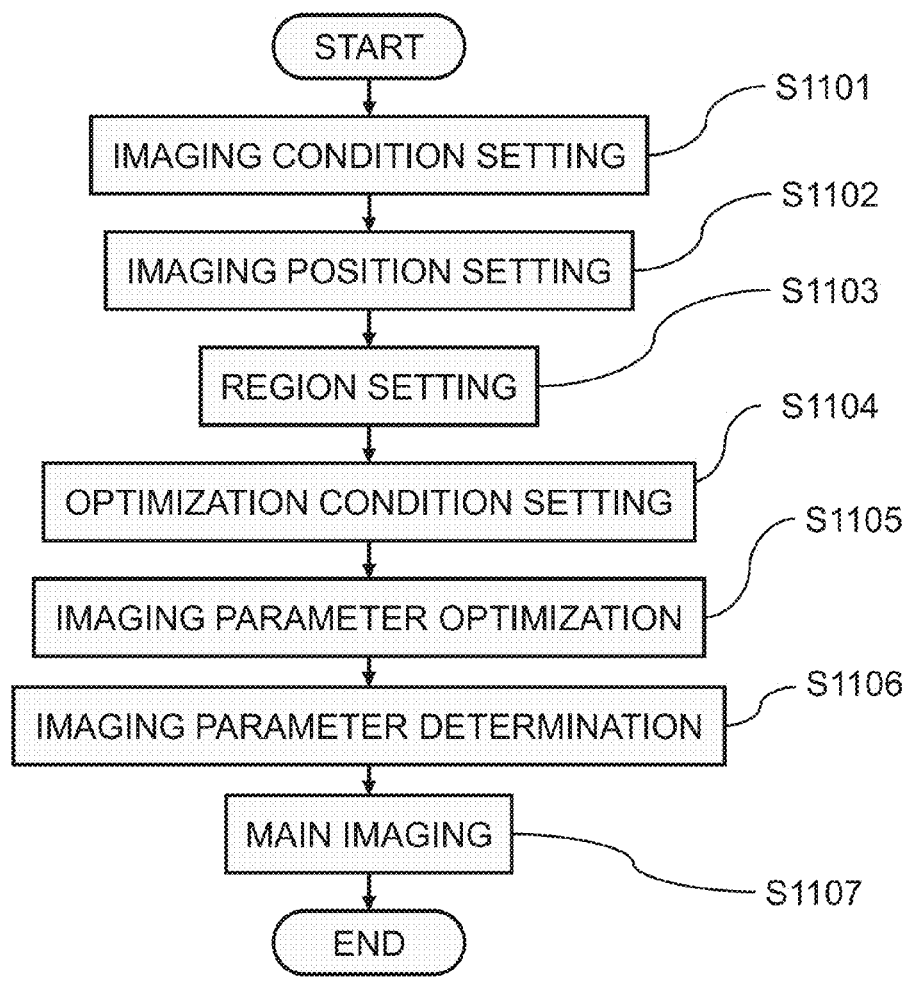
FIG. 7 is a flowchart illustrating an imaging process of the first embodiment.

The flow of an imaging process including the RF shimming process of this embodiment based on the respective functions is shown in FIG. 7. The imaging process of this embodiment is started by an instruction of the user.

First, the imaging parameter determiner 310 receives and sets inputs of imaging conditions including patient information, an imaging portion, an imaging purpose, imaging parameters and the like from a user (step S1101). Then, the imaging position setter 311 performs scout scanning to set an imaging position (step S1102). Thereafter, the region setter 301 sets a first region ROI1 and a second region ROI2 (step S1103). As described above, the second region ROI2 may not be set.

Then, the condition setter 302 extracts and sets optimization conditions including a set of an objective function and a restriction condition from the condition storage 304 (step S1104). The imaging parameter optimizer 303 performs an optimization process of obtaining RF parameters for minimizing the objective function under the restriction condition set by the condition setter 302 (step S1105). Further, the imaging parameter determiner 310 determines the obtained RF parameters as imaging parameters which are an amplitude and a phase of an RF to be transmitted to each channel used for imaging, and sets the imaging parameters together with other imaging parameters as imaging conditions (step S1106).

Further, the imaging unit 320 performs main imaging according to the imaging conditions set by the imaging parameter determiner 310 (step S1107).

The respective functions realized by the computer 109 are realized as a CPU provided in the computer 109 loads a program stored in the storage device 111 in advance to a memory and executes the program, for example. Further, the condition storage 304 and the database 305 are built on the storage device 111. Further, the entirety or some of the functions may be realized by hardware such as an application specific integrated circuit (ASIC) or a field-programmable gate array (FPGA). Further, a variety of data used in processing of the respective functions, and a variety of data generated during the processing are stored in the storage device 111.

Then, a specific example of optimization conditions (a set of an objective function and a restriction condition) stored in the condition storage 304 of this embodiment will be described. In this embodiment, any one of the uniformity of the $B_1$ distribution in the region of interest ROI, emission power that affects an SAR, a $B_1$ average value in the region of interest ROI, and a $B_1$ average value in a region where an artifact is generated in the region of interest is used as an objective function and a restriction condition according to an imaging portion and an imaging purpose. Further, a condition where a local SAR is equal to or smaller than a regulated value is used as a restriction condition.

Hereinafter, in this embodiment, as an index indicating the uniformity of the $B_1$ distribution in a predetermined region, a $B_1$ distribution uniformity index $U_{SD}$ represented by the following Expression (3) is used. The $B_1$ distribution uniformity index $U_{SD}$ is a value obtained by dividing a reference deviation (dev($B_1$)) of the $B_1$ value in the predetermined region by an average value of the $B_1$ value (mean ($B_1$)). It can be said that as the $B_1$ distribution uniformity index $U_{SD}$ is small, the $B_1$ distribution in the region is uniform.

[Expression 3]

$$U_{SD} = \frac{dev(B_1)}{mean(B_1)} \quad (3)$$

First, first optimization condition will be described.

In the first optimization condition, an index for specifying emission power by an RF transmitted to each channel of the transmission coil 114 is used as the objective function. Specifically, an emission power index $P_{SUM}$ represented by the following Expression (4) is used. The emission power index $P_{SUM}$ is the sum of squares of amplitudes of the RF transmitted to each channel.

$$P_{SUM} = A1^2 + A2^2 + A3^2 + A4^2 \quad (4)$$

Further, as restriction conditions, a uniform restriction condition where the uniformity of the $B_1$ distribution is equal to or smaller than a predetermined value, and a local SAR restriction condition where a maximum value of an SAR is equal to or smaller than a predetermined regulated value are used.

The uniformity restriction condition is a condition where a $B_1$ distribution uniformity index $U_{SD\_ROI1}$ in the first region ROI1 is equal to or smaller than a predetermined value $U_U$. Specifically, the uniformity restriction condition is a condition represented by the following Expression (5).

$$U_{SD\_ROI1} \leq U_U \quad (5)$$

The predetermined value Uu for regulating the uniformity of the $B_1$ distribution is set to a value capable of realizing a predetermined image quality in advance, and is stored in the condition storage 304 together with the optimization conditions.

The local SAR restriction condition is a condition where a maximum value (max ($SAR_{dis}$)) of the calculated SAR distribution ($SAR_{dis}$) is equal to or smaller than a predetermined regulated value ($SAR_u$). The local SAR condition is represented by the following Expression (6).

$$\max(SAR_{dis}) \leq SAR_U \quad (6)$$

The regulated value $SAR_U$ for restricting the local SAR is a maximum allowable value of the local SAR. The regulated value $SAR_u$ is set in advance, and is stored in the condition storage 304 together with the optimization conditions.

Accordingly, after the first optimization condition is set as the optimization conditions by the condition setter 302, the imaging parameter optimizer 303 calculates RF parameters as an optimal solution of the following Expression (7). Here, min(x) means minimization of x.

[Expression 7]

$$\min(P_{SUM}) \quad \text{subject to} \begin{Bmatrix} U_{SD\_ROI1} \leq U_U \\ \max(SAR_{dis}) \leq SAR_U \end{Bmatrix} \quad (7)$$

If the first optimization condition is selected and the RF parameters are determined, the $B_1$ distribution uniformity index $U_{SD}$ in the first region ROI1 which is the region of interest is suppressed to be equal to or smaller than a predetermined value by the uniformity restriction condition. Further, in any region, the SAR value does not exceed an allowable value by the local SAR restriction condition. That is, the local SAR can be also controlled.

Accordingly, the first region ROI1 has a uniformity of a predetermined value or greater. Further, since power $P_{SUM}$ of an RF emitted through each channel becomes minimum, emission power with respect to the entire imaging region 201 becomes minimum, to thereby make it possible to suppress the SAR. Further, here, an SAR that is locally generated does not exceed a regulated value.

Particularly, when a region other than the region of interest is a region where an artifact is not generated, it is possible to effectively suppress an SAR while maintaining image quality in the region of interest. In this case, the second region ROI2 may not be selected.

Next, second optimization condition will be described.

An objective function of the second optimization condition is represented by the following Expression (8). The ratio of a $B_1$ average value mean($B_{1\_ROI2}$) in the second region ROI2 to a $B_1$ average value mean($B_{1\_ROI1}$) in the first region ROI1 is represented as $m_{ratio}$. As shown in Expression (8), $m_{ratio}$ is a value obtained by dividing the $B_1$ average value mean ($B_{1\_ROI2}$) in the second region ROI2 by the $B_1$ average value mean ($B_{1\_ROI1}$) in the first region ROI1. Hereinafter, $m_{ratio}$ is referred to as a $B_1$ ratio.

[Expression 8]

$$m_{ratio} = \frac{mean(B_{1\_ROI2})}{mean(B_{1\_ROI1})} \quad (8)$$

Further, as restriction conditions, three conditions, that is, a uniformity restriction condition represented by Expression (5), an emission power restriction condition that an emission power index $P_{SUM}$ in an imaging region is equal to or smaller than a predetermined value $P_U$, and a local SAR restriction condition represented by Expression (6) are used.

The emission power restriction condition is represented by the following Expression (9).

$$P_{SUM} \leq P_U \quad (9)$$

The predetermined value $P_U$ of the emission power restriction condition is determined in advance in terms of safety or the like, and is stored in the condition storage 304 together with the optimization conditions.

Accordingly, after the second optimization condition is set as the optimization conditions by the condition setter 302, the imaging parameter optimizer 303 calculates RF parameters as an optimal solution of the following Expression (10).

[Expression 10]

$$\min(m_{ratio})$$
$$\text{subject to} \begin{cases} P_{SUM} \leq P_U \\ U_{SD\_ROI1} \leq U_U \\ \max(SAR_{dis}) \leq SAR_U \end{cases} \quad (10)$$

$B_1$ represents sensitivity in each region. By relatively suppressing the sensitivity in a suppression region, a signal intensity in the suppression region with respect to a signal intensity in the region of interest is reduced. Accordingly, if the second optimization condition is selected and the RF parameters are determined, since the $B_1$ ratio becomes minimum, it is possible to suppress a signal from the second region ROI2, and to relatively increase a signal from the first region ROI1. Further, the $B_1$ distribution uniformity in the first region ROI1 and the emission power in the imaging region 201 are suppressed to be equal to or smaller than a predetermined value, respectively. Accordingly, it is possible to image the region of interest with high image quality, and to suppress the SAR. Further, since it is possible to suppress a signal value in the suppression region, it is possible to reduce an artifact in the region of interest, and to obtain an image with higher image quality. In addition, it is also possible to appropriately control a local SAR, similar to the first optimization condition.

Particularly, if the second optimization condition is used, when a portion in the vicinity a portion where an artifact is easily generated is an object to be diagnosed, it is possible to effectively suppress an SAR of the whole body while maintaining image quality of the region of interest and satisfying a regulation of a local SAR.

The second optimization condition may be stored in the condition storage 304 in association with the abdomen which is an imaging portion, for example. As described above, since a signal intensity from fat is greater than that of a different tissue, contribution to a physical motion artifact is great. Accordingly, when the abdomen is imaged, a region (fat region) where a large amount of fat is present in an upper portion of the abdomen is set as the second region ROI2, and the RF parameters are determined according to the second optimization condition, and thus, it is possible to reduce a signal value in the fat region, and to safely reduce an artifact.

Figure 8:
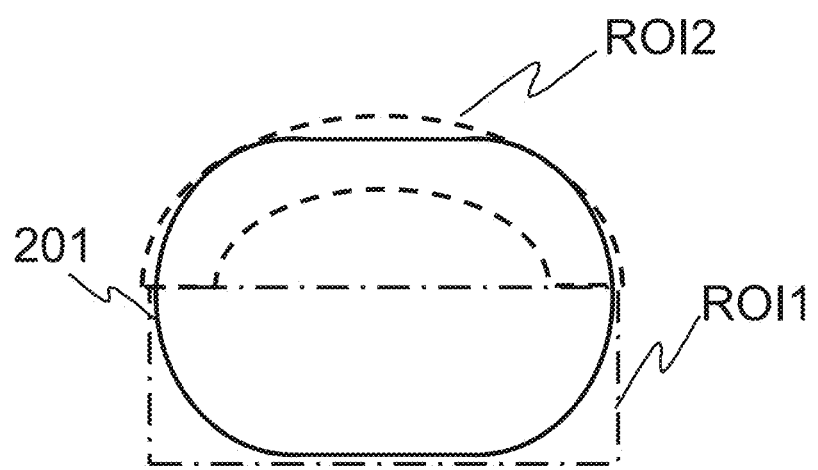
FIG. 8 is a diagram illustrating a setting example of a first region and a second region in imaging the abdomen in the first embodiment.

Here, by selecting the fat region with high accuracy and setting the fat region as the second region ROI2, it is possible to more effectively reduce the $B_1$ ratio of the fat region. Here, a setting example of the first region ROI1 and the second region ROI2 when imaging the abdomen is shown in FIG. 8. An upper surface of the abdomen is a region where a large amount of fat is present. Accordingly, the region of the upper surface of the abdomen is set as the second region ROI2. In this way, by defining the range of the second region ROI2 with high accuracy, it is possible to effectively reduce only a specific region where a signal value is to be reduced. As a method of selecting the fat region, a user may designate a fat region using an image where water and fat are separated from each other, or a computer may automatically designate the fat region.

Next, third optimization condition will be described.
An objective function of the third optimization condition is set to a $B_1$ ratio represented by Expression (8). Further, as restriction conditions, three conditions, that is, a uniformity restriction condition represented by Expression (5), a first region magnetic field restriction condition that a $B_1$ average value mean($B_{1\_ROI}$) in the first region ROI1 is equal to or greater than a predetermined value $B_L$, and a local SAR restriction condition represented by Expression (6) are used.

The first region magnetic field restriction condition is represented by the following Expression (11).

$$\text{mean} B_{1\_ROI1} \geq B_L \quad (11)$$

Here, the predetermined value $B_L$ of the first region magnetic field restriction condition is determined in advance, and is stored in the condition storage 304 together with the optimization conditions.

Accordingly, after the third optimization condition is set as the optimization conditions by the condition setter 302, the imaging parameter optimizer 303 calculates RF parameters as a solution of the following Expression (12).

[Expression 12]

$$\min(m_{ratio})$$
$$\text{subject to} \begin{cases} U_{SD\_ROI1} \leq U_U \\ \text{mean} B_{1\_ROI1} \geq B_L \\ \max(SAR_{dis}) \leq SAR_U \end{cases} \quad (12)$$

If the third optimization condition is selected and the RF parameters are determined, since the $B_1$ ratio is set to minimum under the condition that the $B_1$ average value is equal to or greater than the predetermined value, it is possible to relatively suppress a signal value in the second region ROI2 while maintaining a signal value in the first region ROI1 to be equal to or greater than a predetermined value. Accordingly, it is possible to effectively suppress an artifact. Further, since the $B_1$ distribution uniformity in the first region ROI1 is maintained to be a predetermined value or greater, a region to be diagnosed is imaged with high image quality. Further, similar to the first optimization condition, is also possible to appropriately control a local SAR.

When a portion where an artifact is easily generated is included in a region out of the region of interest of the imaging region 201 by a periodic physical motion, for example, the third optimization condition may be applied by setting a portion that performs the periodic physical motion as the second region ROI2. Accordingly, the third optimization condition may be stored in the condition storage 304 in association with the breast which is an imaging portion. This is because in imaging the breast, the heart that performs the periodical physical motion is included in the imaging region.

FIG. 9(A) is a diagram illustrating the imaging region 201 in imaging the breast. The imaging region 201 is specified by an imaging position (imaging section) set by the imaging position setter 311. Further, FIG. 9(B) is a diagram illustrating the first region ROI1 and the second region ROI2 set by the region setter 301. As shown in the figure, a breast region is set as the first region ROI1, and a heart region is set as the second region ROI2.

By transmitting an RF having an amplitude and a phase calculated according to the third optimization condition through each channel, $B_1$ uniformity in the breast region (first region ROI1) is enhanced, and a signal value of a predetermined value or greater is obtained. On the other hand, it is possible to suppress a signal value in the heart region (second region ROI2). Further, it is also possible to prevent an SAR from locally exceeding a regulated value.

Accordingly, it is possible to safely obtain an image with high image quality in which an artifact in the breast region is reduced.

Next, fourth optimization condition will be described.

An object function of the fourth optimization condition is set as a reciprocal ($1/\text{mean}(B_{1\_ROI1})$) of a $B_1$ average value in the first region ROI1. Further, as restriction conditions, three conditions, that is, a uniformity restriction condition represented by Expression (5), a second region magnetic field restriction condition that a $B_1$ average value mean ($B_{1\_ROI2}$) in the second region ROI2 is equal to or smaller than a predetermined value $B_U$, and a local SAR restriction condition represented by Expression (6) are used.

The second region magnetic field restriction condition is represented by the following expression (13).

$$\text{mean}(B_{ROI2}) \leq B_U \tag{13}$$

Here, the predetermined value $B_U$ is stored in the condition storage 304 together with the optimization conditions.

Accordingly, after the fourth optimization condition is set as the optimization conditions by the condition setter 302, the imaging parameter optimizer 303 calculates RF parameters as a solution of the following Expression (14).

[Expression 14]

$$\min\left(\frac{1}{\text{mean}(B_{1\_ROI1})}\right) \\ \text{subject to } \begin{cases} U_{SD\_ROI1} \leq U_U \\ \text{mean}(B_{1\_ROI2}) \leq B_U \\ \max(SAR_{dis}) \leq SAR_U \end{cases} \tag{14}$$

According to the fourth optimization condition, with respect to the region of interest (first region ROI1), the RF parameters are determined so that a $B_1$ average value becomes maximum while the uniformity of the $B_1$ distribution is maintained to be a predetermined value or greater. Further, with respect to a suppression region (second region ROI2), the RF parameters are determined so that the $B_1$ average value is equal to or smaller than the predetermined value. Similar to the first optimization condition, a local SAR can also be appropriately suppressed.

Accordingly, a signal value from the suppression region is safely suppressed, an artifact is reduced, and image quality in the region of interest is enhanced. The objective function in this case is not limited to the above-described objective function. Any objective function in which an artifact is reduced may be used.

The fourth optimization condition may be applied to off-center imaging in which the center of the subject 103 is deviated from the center of a magnetic field. Accordingly, the fourth optimization condition may be stored in the condition storage 304 in association with the shoulder which is an imaging portion, for example.

FIG. 10(A) is a diagram illustrating the imaging region 201 in imaging the shoulder. The imaging region 201 is specified by an imaging position (imaging section) set by the imaging position setter 311. Further, FIG. 10(B) is a diagram illustrating the first region ROI1 and the second region ROI2 set by the region setter 301 in this case. As shown in the figure, a shoulder which is an imaging object is set as the first region ROI1, and the other shoulder is set as the second region ROI2.

In imaging the shoulder, as described above, since the shoulder which is the imaging object is imaged with high image quality, off-center imaging in which the subject 103 is disposed so that the shoulder to be imaged is positioned at the center (center of the magnetic field) of the transmission coil 114 is performed. Accordingly, as shown in FIG. 10(B), the shoulder region which is not the imaging object is disposed in the vicinity of the transmission coil 114, and a local SAR tends to increase.

Fifth optimization conditions suitable for such a case will be described.

In the fifth optimization conditions, it is a purpose to reduce a local SAR in a region in which the local SAR is considered to be highest. Accordingly, as restriction conditions, a uniformity restriction condition represented by Expression (5), a local power restriction condition that an emission power of an RF transmitted through a channel close to a region where the local SAR is to be reduced, that is, a channel in the vicinity of the second region is equal to or smaller than a predetermined value, and a local SAR restriction condition represented by Expression (6) are used. An objective function is the same as that of the fourth optimization condition.

The fifth optimization conditions may be stored in association with the shoulder.

For example, as shown in FIG. 10(B), when channels close to a region where the local SAR is to be reduced are set to the channel ch2 and the channel ch3, the sum ($A2^2 + A3^2$) of emission powers of the channels is equal to or smaller than a predetermined value $A_U$. The predetermined value $A_U$ is determined in advance, and is stored in the condition storage 304 together with the optimization conditions.

Accordingly, in this case, after the fifth optimization conditions are set as the optimization conditions by the condition setter 302, the imaging parameter optimizer 303 determines an amplitude and a phase of an RF to be transmitted through each channel, as a solution of the following Expression (15).

[Expression 15]

$$\min\left(\frac{1}{\text{mean}(B_{1\_ROI1})}\right) \\ \text{subject to } \begin{cases} U_{SD\_ROI1} \leq U_U \\ A2^2 + A3^2 \leq A_U \\ \max(SAR_{dis}) \leq SAR_U \end{cases} \tag{15}$$

Next, sixth optimization conditions will be described.

Similar to the fifth optimization conditions, a purpose of the sixth optimization conditions is to reduce a local SAR in a region in which the local SAR is considered to be highest. To this end, an objective function is set to the sum of emission powers of an RF transmitted through channels close to a region (second region ROI2) where the local SAR is to be reduced. Further, as restriction conditions, a uniformity restriction condition represented by Expression (5), a restriction condition that an SAR ($SAR_{ROI2}$) in the second region ROI2 is equal to or smaller than a regulated value SAR which is determined in advance, and an SAR restriction condition represented by Expression (6).

The sixth optimization conditions may be stored in association with the shoulder.

The restriction condition that the SAR ($SAR_{ROI2}$) in the second region ROI2 is equal to or smaller than the regulated value SAR is represented by the following Expression (16).

$$SAR_{ROI2} \leq SAR_U \tag{16}$$

The value used in restriction may be a value different from the regulated value $SAR_U$. In this case, the value for regulating the SAR in the second region ROI2 is determined in advance, and is stored in the condition storage 304 together with the optimization condition.

Accordingly, after the sixth optimization conditions are set as the optimization conditions by the condition setter 302, the imaging parameter optimizer 303 determines RF parameters as a solution of the following Expression (17). Here, for example, channels close to a region where the local SAR is to be reduced are set to the channel ch2 and the channel ch3.

[Expression 17]

$$\min(A2^2 + A3^2) \\ \text{subject to} \begin{cases} U_{SD\_ROI1} \le U_U \\ SAR_{ROI2} \le SAR_U \\ \max(SAR_{dis}) \le SAR_U \end{cases} \quad (17)$$

Here, the SAR in the second region ROI2 is estimated from a $B_1$ distribution, for example. Further, the SAR may be calculated using an electromagnetic field simulation. When the SAR is calculated using the electromagnetic field simulation, for example, a method of using a result obtained by calculating an SAR distribution in a physical body model may be used.

When the shoulder which is an imaging object is set as the first region ROI1 and a region of the other shoulder close to the transmission coil 114 is set as the second region ROI2, by transmitting the RF having the amplitude and the phase calculated according to the fifth or sixth optimization conditions through each channel, it is possible to suppress emission power in the vicinity of the other shoulder region (second region ROI2) while maintaining the $B_1$ uniformity in the shoulder region which is the imaging object (first region ROI1) to a predetermined value and satisfying a regulation of a local SAR.

Accordingly, if the fifth or sixth optimization conditions are selected and the RF parameters are determined, since the $B_1$ uniformity in the region of interest is maintained to be a predetermined value or greater and the emission power in the vicinity of the suppression region is suppressed, it is possible to safely achieve enhancement of the image quality in the region of interest and reduction of the local SAR.

Next, seventh optimization conditions will be described.

An objective function of the seventh optimization conditions uses an index obtained by combining a weighted emission power index $P_{SUM}$ and a weighted $B_1$ ratio, represented by the following Expression (18). Hereinafter, this index is called the combined index.

$$\alpha P_{SUM} + \beta m_{ratio} \quad (18)$$

Here, $\alpha + \beta = 1$. Further, $\alpha$ and $\beta$ are set by a user according to their importance levels. Alternatively, $\alpha$ and $\beta$ may be set in advance for each imaging portion.

As restriction conditions, a uniformity restriction condition represented by Expression (5), and a local SAR restriction condition represented by Expression (6) are used.

Accordingly, after the seventh optimization conditions are set as the optimization conditions by the condition setter 302, the imaging parameter optimizer 303 calculates RF parameters as an optimal solution of the following Expression (19).

[Expression 19]

$$\min(\alpha P_{SUM} + \beta m_{ratio}) \\ \text{subject to} \begin{cases} U_{SD\_ROI1} \le U_U \\ \max(SAR_{dis} \le SAR_U) \end{cases} \quad (19)$$

If the seventh optimization conditions are selected and the RF parameters are determined, respective effects are obtained when selecting the first optimization condition and when selecting the second optimization condition. Further, the degrees of the effects may be adjusted by coefficients to be set.

The optimization conditions stored in the condition storage 304 are not limited to the above-described seven conditions. Any other conditions capable of obtaining a solution for setting the uniformity of the $B_1$ distribution in the first region ROI1 which is the region of interest to be a predetermined level or higher, effectively realizing at least one of reduction of an artifact and suppression of a whole body SAR, and reducing a local SAR may be used. In addition, any other conditions capable of obtaining a solution for appropriately controlling a local SAR, setting at least one of the level of an artifact and the level of a whole body SAR to be a predetermined value or smaller, and realizing enhancement of the uniformity of the $B_1$ distribution in the first region ROI1 may be used.

As described above, the MRI device 100 of this embodiment includes the transmission coil 114 that has plural channels and respectively transmits radio frequency pulses to the subject 103, the imaging parameter determiner 310 that determines predetermined imaging parameters among imaging conditions used when the subject 103 is imaged, and the imaging unit 320 that executes imaging using the determined imaging parameters. Further, the imaging parameter determiner 310 includes the database 305 that retains data capable of calculating a specific absorption rate distribution for each subject model which is determined in advance, and the imaging parameter optimizer 303 that determines imaging parameters that optimize a radio frequency magnetic field distribution in an imaging region while suppressing a maximum value of a local specific absorption rate to be equal to or smaller than a predetermined specific absorption rate threshold value using the data in the database 305. The imaging parameters determined by the imaging parameter optimizer 303 include a radio frequency magnetic field parameter (RF parameter) for specifying the radio frequency pulses transmitted through the plural channels.

Further, the imaging parameter optimizer 303 determines the radio frequency magnetic field parameter according to predetermined optimization conditions, and the optimization conditions include a uniformity condition that the uniformity of the radio frequency magnetic field distribution is equal to or greater than a predetermined value, and a local specific absorption rate condition that the maximum value of the local specific absorption rate is equal to or smaller than the specific absorption rate threshold value, as restriction conditions.

Further, the radio frequency magnetic field parameter is set to be at least one of the amplitude and the phase of the radio frequency pulses transmitted through each of the plural channels of the transmission coil 114.

In addition, the data retained in the database 305 is an electric field distribution for each of the plural channels, for each subject model, and the electric field distribution is a distribution when radio frequency magnetic field pulses having an amplitude and a phase which are a predetermined reference in imaging one piece of slice is emitted once per unit time.

The predetermined imaging parameters are determined so that the high frequency magnetic field distribution in the imaging region is optimized while suppressing the maximum value of the local specific absorption rate to be equal to or smaller than the predetermined specific absorption rate threshold value using predetermined data in the database. The imaging parameters include the radio frequency magnetic field parameter for specifying the radio frequency pulses to be transmitted through each of the plural channels of the transmission coil of the magnetic resonance imaging device. The data retained in the database is data capable of calculating the specific absorption rate distribution for each subject model. The radio frequency magnetic field parameter is determined according to the optimizations conditions including the uniformity condition that the uniformity of the radio frequency magnetic field distribution is equal to or greater than the predetermined value and the local specific absorption rate condition that the maximum value of the local specific absorption rate is equal to or smaller than the specific absorption rate threshold value as the restriction conditions.

As described above, according to this embodiment, at least one of the amplitude and the phase of the RF pulses to be transmitted through each channel is determined so that the $B_1$ distribution uniformity index $U_{SD}$ in the first region ROI1 which is a region (region of interest) to be diagnosed is suppressed to a predetermined value or smaller while appropriately controlling a local SAR. Further, in this imaging, RF pulses are emitted using the determined amplitude and phase.

Accordingly, in the first region ROI1, a predetermined uniformity can be maintained. Further, the power $P_{SUM}$ of the RF emitted through each channel is minimized or suppressed to a predetermined value or smaller according to the optimization conditions while appropriately controlling a local SAR. Accordingly, it is possible to suppress an SAR. In addition, for example, in a region other than the region of interest, the second region ROI2 is set as necessary, and a $B_1$ value or emission power in this region is reduced while appropriately controlling a local SAR. For example, if a region where contribution to generation of an artifact is great is set as the second region ROI2 and a $B_1$ value is reduced, it is possible to reduce the artifact with high efficiency. Further, if a region where a high SAR is locally generated is set as the second region ROI2 and emission power is reduced, it is possible to reduce a local SAR with high efficiency.

Further, in this embodiment, one amplitude and one phase are determined with respect to RF pulses emitted through each channel in one-time imaging. Accordingly, regardless of whether an imaging sequence is a single shot or multi-shot, the above-described effects can be obtained. Further, even though the imaging sequence is the multi-shot, since the amplitude and the phase of the RF pulses are not changed between shots, complicated processing is not necessary.

Accordingly, according to this embodiment, in the MRI device using the transmission coil having the plural channels, it is possible to determine RF parameters for imaging a region to be diagnosed with high image quality while appropriately controlling a local SAR and reducing at least one of a whole body SAR and an artifact. Further, since the imaging is performed using the RF parameters, it is possible safely and efficiently to acquire an image having high image quality in the region to be diagnosed with a simple configuration, regardless of the imaging sequence.

Second Embodiment

A second embodiment of the invention will be described. In this embodiment, RF parameters are determined so that at least one of a whole body SAR and an artifact is suppressed and a high quality image in a region of interest ROI is efficiently obtained, and then, a local SAR is confirmed. When a maximum value of the local SAR exceeds a regulated value, a parameter other than the RF parameters is adjusted, and thus, the local SAR is controlled. The adjusted parameter refers to a parameter that affects an SAR among parameters set as imaging conditions.

Hereinafter, the parameter which is the parameter other than the RF parameters and affects the SAR among the parameters set as the imaging parameters is referred to as an SAR parameter. For example, the set imaging parameters include a TR, a TE, a field of view (FOV), a matrix size, a flip angle (FA), a slice thickness, the number of slices, a slice interval, and the like.

As described above, an SAR distribution is calculated from an expression for each slice per unit time. Accordingly, the SAR parameters include a TR (repetition time) and the number of slices that regulate the SAR parameters.

The MRI device of this embodiment has basically the same configuration as that of the MRI device 100 of the first embodiment. Here, as described above, since this embodiment is different from the first embodiment in an RF parameter optimization method and a local SAR control method, processes in the imaging parameter optimizer 303 and a configuration thereof are different. Hereinafter, in this embodiment, different configurations from those of the first embodiment are mainly described.

The RF shimming part 313 of this embodiment first calculates RF parameters according to optimization conditions setting a $B_1$ distribution uniformity in the region of interest (first region ROI1) to be equal to or greater than a predetermined value and reducing at least one of a whole body SAR and an artifact. Further, the RF shimming part 313 calculates an SAR distribution using the obtained RF parameters. When a maximum value of the SAR distribution exceeds a regulated value, the RF shimming part 313 adjusts the SAR parameters to suppress the SAR distribution to be equal to or smaller than the regulated value.

Figure 11:
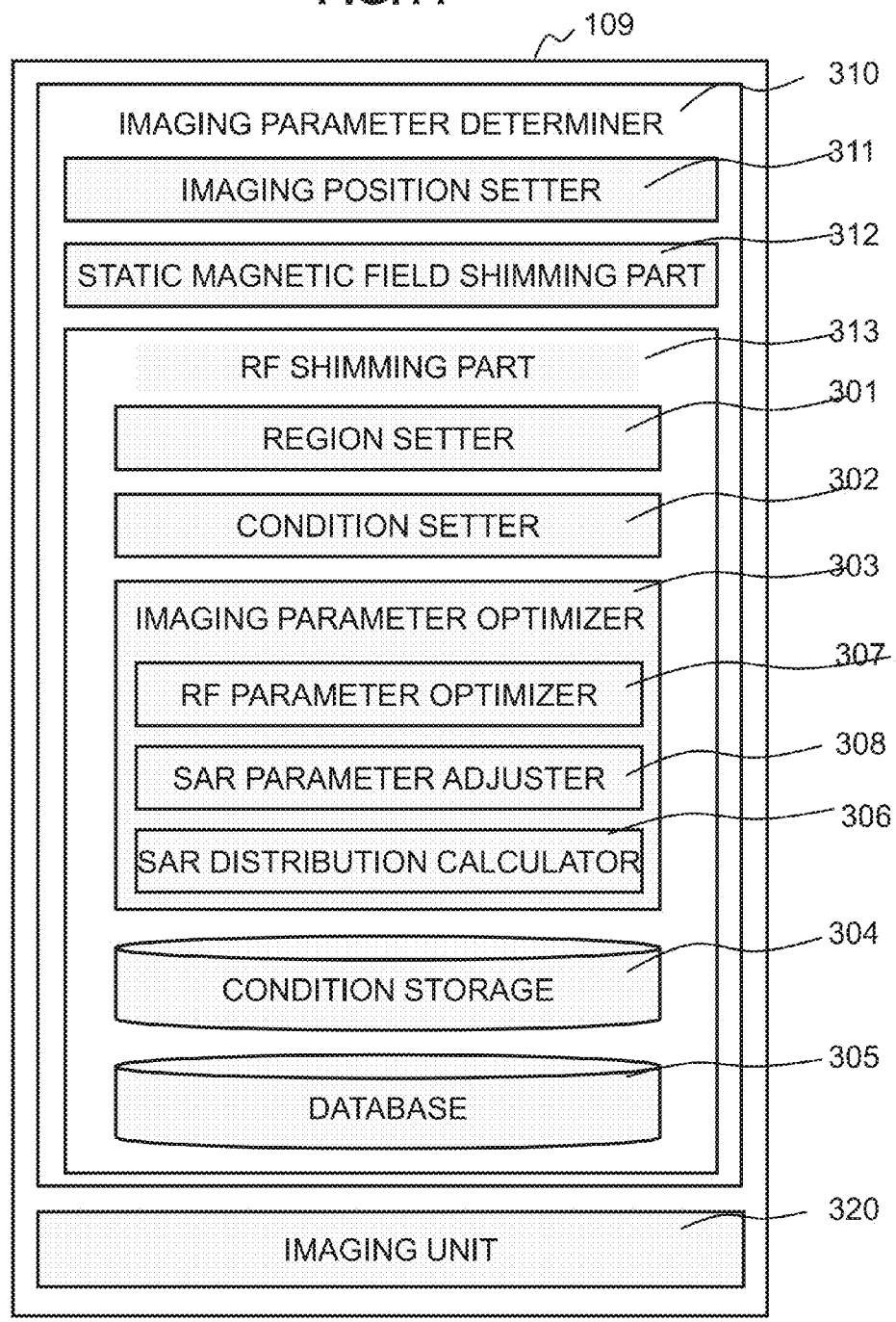
FIG. 11 is a functional block diagram illustrating a computer of a second embodiment.

Accordingly, the imaging parameter optimizer 303 of this embodiment further includes an RF parameter optimizer 307 and an SAR parameter adjuster 308, as shown in FIG. 11.

The RF parameter optimizer 307 optimizes and determines RF parameters according to predetermined optimization conditions.

The optimization conditions used in this embodiment do not include a local SAR restriction condition. For example, the first to seventh optimization conditions of the first embodiment are represented by the following Expression (20) to Expression (26), respectively.

[Expression 20]

$$\left.\begin{array}{l}\min(P_{SUM}) \\ \text{subject to } U_{SD\_ROI1} \leq U_U\end{array}\right\} \quad (20)$$

-continued

[Expression 21]

$$\min(m_{ratio}) \quad \text{subject to} \begin{cases} P_{SUM} \leq P_U \\ U_{SD\_ROI1} \leq U_U \end{cases} \quad (21)$$

[Expression 22]

$$\min(m_{ratio}) \quad \text{subject to} \begin{cases} U_{SD\_ROI1} \leq U_U \\ \text{mean}B_{1\_ROI1} \geq B_L \end{cases} \quad (22)$$

[Expression 23]

$$\min\left(\frac{1}{\text{mean}(B_{1\_ROI1})}\right) \quad \text{subject to} \begin{cases} U_{SD\_ROI1} \leq U_U \\ \text{mean}(B_{1\_ROI2}) \leq B_U \end{cases} \quad (23)$$

[Expression 24]

$$\min\left(\frac{1}{\text{mean}(B_{1\_ROI1})}\right) \quad \text{subject to} \begin{cases} U_{SD\_ROI1} \leq U_U \\ A2^2 + A3^2 \leq A_U \end{cases} \quad (24)$$

[Expression 25]

$$\min(A2^2 + A3^2) \quad \text{subject to } U_{SD\_ROI1} \leq U_U \quad (25)$$

[Expression 26]

$$\min(\alpha P_{SUM} + \beta m_{ratio}) \quad \text{subject to } U_{SD\_ROI1} \leq U_U \quad (26)$$

In this embodiment, similarly, the optimization conditions are stored in the condition storage 304 in advance.

The SAR parameter adjuster 308 determines whether the SAR distribution ($SAR_{dis}$) calculated by the SAR distribution calculator 306 using the optimized RF parameters satisfies a regulation of an SAR. When the SAR distribution ($SAR_{dis}$) does not satisfy the regulation of the SAR, the SAR parameter adjuster 308 adjusts the SAR parameters.

In each time of calculation of the SAR distribution ($SAR_{dis}$) the SAR parameter adjuster 308 determines whether a maximum value (max($SAR_{dis}$)) of the obtained SAR distribution ($SAR_{dis}$) does not exceed a predetermined regulated value ($SAR_U$). When the maximum value (max($SAR_{dis}$)) does not exceed the predetermined regulated value ($SAR_{dis}$), that is, when the maximum value (max($SAR_{dis}$)) satisfies the following Expression (27), the SAR parameter adjuster 308 does not change the SAR parameters.

$$\max(SAR_{dis}) \leq SAR_U \quad (27)$$

On the other hand, when the maximum value (max($SAR_{dis}$)) exceeds the predetermined regulated value ($SAR_{dis}$), the SAR parameter adjuster 308 changes the SAR parameters so that the maximum value (max($SAR_{dis}$)) of the SAR distribution ($SAR_{dis}$) does not exceed the regulated value $SAR_U$.

In this embodiment, at least one of a TR that affects the number n of applied RF pulses per unit time and the number m of slices is changed according to Expression (2).

For example, the maximum value (max($SAR_{dis}$)) of the SAR distribution ($SAR_{dis}$) is a value greater than the regulated value SAR by p times, the TR is set to p times, or the number of slices is set to 1/p times, for example. Parameters to be changed may be determined in advance. Further, a user may designate the parameters.

When the user designates the parameters, the SAR parameter adjuster 308 shows the user what times the maximum value (max($SAR_{dis}$)) of the SAR is greater than the regulated value ($SAR_U$), and the user performs change into a desired imaging condition according to the result. The imaging condition to be changed may be plural. In this case, for example, the TR may be set to p/2 times, and the number of slices may be set to 2/p times.

The SAR distribution ($SAR_{dis}$) is calculated by the SAR distribution calculator 306, similar to the first embodiment. Specifically, if optimization of the RF parameters is performed using any one of the respective optimization conditions, the SAR distribution calculator 306 accesses the database 305 to extract a record that matches the set imaging conditions. Further, the SAR distribution calculator 306 calculates the SAR distribution ($SAR_{dis}$) according to Expression (2) using the optimized RF parameters, the imaging conditions, and a value of the record.

The flow of imaging processes of this embodiment is basically the same as that of the first embodiment. However, this embodiment is different from the first embodiment in an imaging parameter optimization process performed by the imaging parameter optimizer 303 in step S1105.

Figure 12:
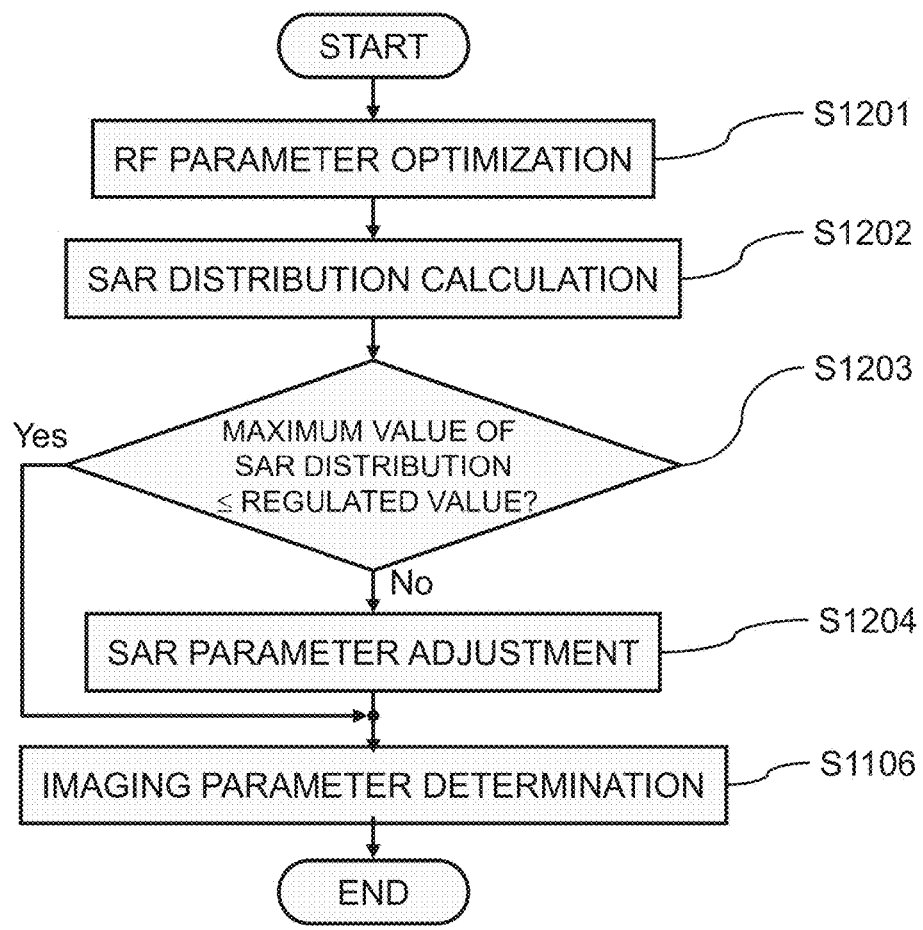
FIG. 12 is a flowchart illustrating an imaging parameter optimization process of the second embodiment.

Hereinafter, the flow of the imaging parameter optimization process of this embodiment will be described. FIG. 12 is a processing flow of the imaging parameter optimization process of this embodiment. This process is started when optimization conditions to be used are set.

The RF parameter optimizer 307 performs an optimization process of calculating a solution for minimizing an objective function under a predetermined restriction condition set by the condition setter 302, and determines RF parameters (step S1201). After the RF parameter optimizer 307 determines the RF parameters, the SAR distribution calculator 306 calculates an SAR distribution (step S1202).

After the SAR distribution is calculated, the SAR parameter adjuster 308 determines whether a maximum value of the SAR distribution is equal to or smaller than a regulated value of an SAR (step S1203). As a determination result, when the maximum value does not exceed the regulated value (is equal to or smaller than the regulated value), the imaging parameter optimizer 303 determines the RF parameters determined in step S1201 and the latest SAR parameters at that time point as the imaging parameters, and sets the imaging parameters together with other imaging parameters as imaging conditions (step S1106).

On the other hand, in step S1203, when it is determined that the maximum value exceeds the regulated value, the SAR parameter adjuster 308 adjusts the SAR parameters by the above-described method, and replaces the SAR parameters with adjusted values (step S1204). Then, the procedure proceeds to step S1106. Here, in step S1106, the adjusted SAR parameters are set as the imaging conditions.

As described above, the MRI device of this embodiment includes the transmission coil 114, the imaging parameter determiner 310, the imaging unit 320, the database 305, and the imaging parameter optimizer 303, similar to the first embodiment.

Further, the imaging parameters determined by the imaging parameter optimizer 303 further include specific absorption rate parameters (SAR parameters) which are imaging parameters that affect a specific absorption rate in addition to the radio frequency magnetic field parameters. Further, the imaging parameter optimizer 303 includes a radio frequency magnetic field parameter optimizer (RF parameter optimizer 307) that determines radio frequency magnetic field parameters according to predetermined optimization conditions, a specific absorption rate distribution calculator (SAR distribution calculator 306) that calculates a specific absorption rate distribution using the determined radio frequency magnetic field parameters, the latest specific absorption rate parameters, and data in the database whenever the radio frequency magnetic field parameters are determined, and a specific absorption rate parameter adjuster (SAR parameter adjuster 308) that determines whether a maximum value of the calculated specific absorption rate distribution exceeds a specific absorption rate threshold value whenever the specific absorption rate distribution is calculated and adjusts, if the maximum value exceeds the specific absorption rate threshold value, the specific absorption rate parameters so that the maximum value of the specific absorption rate distribution is equal to or smaller than the specific absorption rate threshold value. Here, the optimization conditions may include a uniformity condition that the uniformity of the radio frequency magnetic field distribution is equal to or greater than a predetermined value as a restriction condition.

In this way, according to this embodiment, it is possible to suppress the $B_1$ distribution uniformity index $U_{SD}$ in the first region ROI1 which is a region to be diagnosed (region of interest) to be equal to or smaller than a predetermined value. Further, it is possible to suppress the power $P_{SUM}$ of RF pulses emitted through respective channels to a minimum value or a predetermined value or smaller according to the optimization conditions. Accordingly, it is possible to suppress an SAR. Further, for example, the second region ROI2 is set in a region out of the region of interest as necessary, and the $B_1$ value or emission power in the region is reduced. For example, a region that greatly contributes to generation of an artifact is set as the second region ROI2, and if the $B_1$ value is reduced, it is possible to reduce the artifact with high efficiency. Further, a region where a high SAR is locally generated is set as the second region ROI2, and if emission power is reduced, it is possible to reduce the local SAR with high efficiency.

Further, the SAR distribution is calculated using the obtained result, and when the SAR distribution exceeds a regulation, imaging parameters other than the RF parameters are adjusted, and thus, a local SAR is adjusted.

Accordingly, according to this embodiment, in the MRI device using the transmission coil having plural channels, it is possible to determine RF parameters for imaging a region to be diagnosed with high image quality while appropriately suppressing a local SAR and reducing at least one of a whole body SAR and an artifact. Further, since the imaging is performed using the RF parameters, similar to the first embodiment, it is possible to safely and efficiently acquire an image of high image quality in the region to be diagnosed with a simple configuration, regardless of an imaging sequence.

Third Embodiment

Next, a third embodiment of the invention will be described. In this embodiment, RF parameters are determined so that at least one of a whole body SAR and an artifact is suppressed and a high quality image in a region of interest ROI is effectively obtained, and a local SAR is confirmed, and when a maximum value thereof exceeds a regulated value, at least one of imaging quality and an imaging time is adjusted.

The MRI device of this embodiment has basically the same configuration as that of the MRI device of the second embodiment. However, this embodiment is different from the second embodiment in processes of the imaging parameter optimizer 303 and the SAR parameter adjuster 308.

In this embodiment, when after the RF parameters are optimized, a regulation of an SAR is not satisfied, SAR parameters are adjusted so that the regulation of the SAR is satisfied, similar to the second embodiment. Here, it is determined whether a total imaging time when imaging is performed using the adjusted SAR parameters is within an allowable range. When the total imaging time is out of the allowable range, parameters relating to image quality are adjusted, and the RF parameters are optimized again.

The parameters relating to image quality is a predetermined value $U_U$ used as a threshold value of restriction conditions relating to the $B_1$ distribution uniformity. Hereinafter, the value $U_U$ is referred to as a uniformity threshold value. In this embodiment, when the total imaging time is out of the allowable range, the uniformity threshold value is changed so that a regulation of the uniformity becomes smooth. When the uniformity threshold value $U_U$ is changed, since a configuration of optimization conditions is changed, it is necessary to perform optimization again. Here, the uniformity threshold value $U_U$ increases by a predetermined amount ($\Delta U$).

To this end, the SAR parameter adjuster 308 of this embodiment includes an imaging time determiner 309, as shown in FIG. 13. After the SAR parameters are adjusted by the same method as in the second embodiment, the imaging time determiner 309 calculates a total imaging time when the adjusted SAR parameters are used. The total imaging time is calculated using imaging conditions. Further, it is determined whether the total imaging time is within an allowable range.

If the total imaging time is within the allowable range, the SAR parameter adjuster 308 outputs the adjusted SAR parameters as an adjustment result.

On the other hand, when the total imaging time is out of the allowable range, the result is output. The imaging parameter optimizer 303 receives the output, changes the uniformity threshold value $U_U$, and makes the RF parameter optimizer 307 optimize the RF parameters again.

The flow of the imaging process of this embodiment is basically the same as in the first embodiment. However, similar to the second embodiment, this embodiment is different from the first embodiment in an imaging parameter optimization process performed by the imaging parameter optimizer 303 in step S1105.

Hereinafter, the flow of the imaging parameter optimization process of this embodiment will be described. FIG. 14 is a processing flow of the imaging parameter optimization process of this embodiment. This process is started when optimization conditions to be used are set.

The RF parameter optimizer 307 performs an optimization process of calculating a solution for minimizing an objective function under a predetermined restriction condition set by the condition setter 302, and determines RF parameters (step S1301). After the RF parameter optimizer 307 determines the RF parameters, the SAR distribution calculator 306 calculates an SAR distribution (step S1302).

After the SAR distribution is calculated, the SAR parameter adjuster 308 determines whether a maximum value of the SAR distribution is equal to or smaller than a regulated value of an SAR (step S1303). As a determination result, when the maximum value does not exceed the regulated value (is equal to or smaller than the regulated value), the imaging parameter optimizer 303 determines the RF parameters determined in step S1301 and the latest SAR parameters at that time point as the imaging parameters, and sets the imaging parameters together with other imaging parameters as imaging conditions (step S1106).

On the other hand, in step S1303, when it is determined that the maximum value exceeds the regulated value, the SAR parameter adjuster 308 adjusts the SAR parameters by the above-described method, and replaces the SAR parameters with adjusted values (step S1304). Then, the imaging time determiner 309 calculates a total imaging time when the adjusted SAR parameters are used (step S1305). Further, the imaging time determiner 309 determines whether the calculated total imaging time is within an allowable range (step S1306).

If the total imaging time is within the allowable range, the procedure proceeds to step S1106. Here, in step S1106, the SAR parameters adjusted in step S1304 are set as the imaging conditions.

On the other hand, in step S1306, when the total imaging time is out of the allowable range, the imaging parameter optimizer 303 increases the uniformity threshold value $U_U$ by a predetermined value $\Delta U (U_U = U_U + \Delta U)$ (step S1307).

Further, the RF parameter optimizer 307 optimizes the RF parameters again using the changed optimization conditions (step S1308). In addition, the SAR distribution calculator 306 calculates an SAR distribution using the optimized RF parameters and the SAR parameters adjusted in step S1304 (step S1309).

The imaging parameter optimizer 303 determines whether the maximum value is equal to or smaller than the regulated value of an SAR (step S1310). As a determination result, when the maximum value is equal to or smaller the regulated value of the SAR, the procedure proceeds to step S1106. Here, in step S1106, the SAR parameters adjusted in step S1304 and the RF parameters optimized in step S1308 are set as the optimization conditions.

On the other hand, when it is determined that the maximum value exceeds the regulated value in step S1310, the imaging parameter optimizer 303 makes the procedure proceed to step S1307, changes the uniformity threshold value $U_U$ again, and repeats the process.

As described above, the MRI device of this embodiment includes the transmission coil 114, the imaging parameter determiner 310, the imaging unit 320, the database 305, and the imaging parameter optimizer 303, similar to the second embodiment. Further, the imaging parameter optimizer 303 includes the radio frequency magnetic field parameter optimizer (RF parameter optimizer 307), the specific absorption rate calculator (SAR distribution calculator 306), and the specific absorption rate parameter adjuster (SAR parameter adjuster 308). The optimization conditions include a uniformity condition that the uniformity of the radio frequency magnetic field distribution is equal to or greater than a predetermined value as a restriction condition. The specific absorption rate parameter adjuster (SAR parameter adjuster 308) includes the imaging time determiner 309 that calculates a time relating to imaging using the adjusted specific absorption rate parameters and determines whether the calculated imaging time is within an allowable range. When it is determined by the imaging time determiner 309 that the calculated imaging time is not within the allowable range, the imaging parameter optimizer 303 changes a threshold value (uniformity threshold value) that regulates the uniformity condition in the optimization conditions by a predetermined value to smooth the uniformity condition, and makes the radio frequency magnetic field parameter optimizer determine the radio frequency magnetic field parameters again.

Thus, according to this embodiment, similar to the second embodiment, in the MRI device using the transmission coil having plural channels, it is possible to determine RF parameters for imaging a region to be diagnosed with high image quality while appropriately suppressing a local SAR and reducing at least one of a whole body SAR and an artifact. Further, since the imaging is performed using the RF parameters, similar to the first embodiment, it is possible to safely and efficiently acquire an image of high image quality in the region to be diagnosed with a simple configuration, regardless of an imaging sequence.

In this embodiment, in the imaging parameter optimization process, the SAR parameter adjuster 308 adjusts the SAR parameters so that the regulation of the local SAR is satisfied, similar to the second embodiment, but the invention is not limited thereto. For example, a configuration in which the SAR parameters are adjusted in a predetermined range may be used. For example, the predetermined range is set to a range within a total imaging time.

Then, after the SAR parameters are adjusted within the range, the SAR distribution is calculated again, and it is determined whether the maximum value exceeds the regulated value. When the maximum value exceeds the regulated value, the uniformity threshold value $U_U$ is changed by the above-described method, and the process is repeated.

That is, if the specific absorption rate parameters are changed, the imaging parameter optimizer 303 makes the SAR distribution calculator 306 calculate the specific absorption rate distribution using the changed specific absorption rate parameters, and determines whether the maximum value of the specific absorption rate distribution calculated using the changed specific absorption rate parameters exceeds the specific absorption rate threshold value. When the maximum value of the specific absorption rate distribution exceeds the specific absorption rate threshold value, the imaging parameter optimizer 303 repeats the process of changing a threshold value for regulating the uniformity condition in the optimization conditions by a predetermined value to smooth the uniformity condition, the process of making the radio frequency magnetic field parameter optimizer (RF parameter optimizer 307) to determine the radio frequency magnetic field parameters again, and the process of making the SAR distribution calculator 306 to calculate the specific absorption rate distribution using the re-determined radio frequency magnetic field parameters, until the maximum value of the specific absorption rate distribution becomes equal to or smaller than the specific absorption rate threshold value.

Hereinafter, the flow of an imaging parameter optimization process of this modification example will be described with reference to FIG. 15.

The RF parameter optimizer 307 performs an optimization process of calculating a solution for minimizing an objective function under a predetermined restriction condition set by the condition setter 302 (step S1401). After the RF parameter optimizer 307 determines RF parameters, the SAR distribution calculator 306 calculates an SAR distribution (step S1402).

After the SAR distribution is calculated, the SAR parameter adjuster 308 determines whether a maximum value of the SAR distribution is equal to or smaller than a regulated value of an SAR (step S1403). As a determination result, when the maximum value does not exceed the regulated value (is equal to or smaller than the regulated value), the imaging parameter optimizer 303 determines the RF parameters determined in step S1301 and the latest SAR parameters at that time point as the imaging parameters, and sets the imaging parameters together with other imaging parameters as imaging conditions (step S1106).

On the other hand, in step S1403, when it is determined that the maximum value exceeds the regulated value, the SAR parameter adjuster 308 adjusts the SAR parameters by the above-described method, and replaces the SAR parameters with adjusted values (step S1404). Then, the SAR parameter adjuster 308 determines whether the adjusted values satisfy the regulation of the SAR using the adjusted values (step S1405). Further, when the adjusted values satisfy the regulation of the SAR, the procedure proceeds to step S1106. Here, in step S1106, the SAR parameters adjusted in step S1404 are determined as the imaging parameters, and are set as the imaging conditions.

On the other hand, in step S1405, when it is determined that the maximum value exceeds the regulated value, the imaging parameter optimizer 303 increases the uniformity threshold value $U_U$ by a predetermined value $\Delta U (U_U = U_U + \Delta U)$ (step S1406).

Further, the RF parameter optimizer 307 optimizes the RF parameters again using the changed optimization conditions (step S1407). Then, the SAR distribution calculator 306 calculates an SAR distribution using the optimized RF parameters and the SAR parameters adjusted in step S1304 (step S1408). Then, the procedure proceeds to step S1405.

In the respective embodiments, an electric field distribution for each physical body model and each channel is retained in the database 305, but the retained data is not limited thereto. For example, the database 305 may retain an SAR distribution, a whole body SAR, a local SAR, and a ratio of maximum values of the whole body SAR and the local SAR for each physical body model, and a $B_1$ distribution for each channel, or the like. The data may be retained in association with a specific emission method. The specific emission method is QD emission which is a representative emission method in four-channel imaging, or the like, for example.

By retaining the data, in the specific emission method, it is possible to reduce the workload of calculating an SAR according to Expression (2), and thus, it is possible to reduce the processing time.

In the above-described embodiments, in the optimization process, the solution for minimizing each objective function is calculated, but the invention is not limited thereto. For example, a configuration in which each objective function is set as a reciprocal of each objective function described above and a solution for maximizing the reciprocal objective function is calculated may be used. Further, a configuration in which a negative sign is assigned to each index and a solution for maximizing the index is calculated may be used.

Further, in the respective embodiments, pre-saturation pulses used for reduction of an artifact may be applied together with RF pulses. For example, when suppressing a signal in an upper half region (second region ROI2) as much as possible while uniformly emitting the RF pulses to a lower half region of a section (first region ROI1), the pre-saturation pulses may be emitted to the upper half region.

When the pre-saturation pulses are emitted to the upper half region which is an emission objective region as uniformly as possible, an artifact reduction effect becomes high. Thus, when emitting the pre-saturation pulses, it is preferable that the RF parameters are calculated so that a $B_1$ distribution in the upper half region becomes as uniform as possible. That is, an objective function is set using a $B_1$ uniformity ($U_{SD\ ROI2}$) in the second region ROI2 as represented by the following Expression (28), and RF parameters for the pre-saturation pulses are calculated.

$$\min(U_{SD\ ROI2}) \tag{28}$$

Next, excitation pulses after application of the pre-saturation pulses are emitted with RF parameters that uniformize a $B_1$ distribution in the lower half region (first region ROI1) as described above. In this way, by respectively applying optimal RF parameters as the pre-saturation pulses and the excitation pulses, the artifact reduction effect becomes higher.

In the respective embodiments, a case where one first region ROI1 which is a region of interest and one second region ROI2 which is a suppression region are respectively set is described as an example, but the invention is not limited thereto. Plural first regions and plural second regions may be respectively set. For example, when plural regions where an artifact is to be reduced are separately present, the first region ROI1 and the second region ROI2 are set for each region. With such a configuration, it is possible to more locally suppress a $B_1$ value, and to effectively reduce the artifact.

Further, here, for example, when restriction conditions for suppressing a $B_1$ average value in the suppression region are set as in the fourth optimization condition, with respect to each of the plural suppression regions, a predetermined value $B_U$ of the restriction conditions may be set as a different value. That is, weighting may be performed with respect to the restriction conditions according to positions of the suppression regions.

In addition, in the respective embodiments, a case where an imaging region is two-dimensional is mainly described as an example, but even when an imaging region is three-dimensional, it is possible to calculate optimal RF parameters by the same method.

Further, in the respective embodiments, a 3 T MRI device and a transmission coil of four channels are described as an example, but the invention is not limited thereto. A transmission coil having a magnetic field higher than 3T and channels greater than four in number may be used.

Furthermore, in the respective embodiments, the computer 109 included in the MRI device 100 is configured to include the RF shimming part 313 so that at least one of an optimal amplitude and an optimal phase of an RF is calculated, but the invention is not limited thereto. For example, the RF shimming part 313 may be provided in a computer independent of the MRI device 100, capable of performing data transmission/reception with the computer 109. Similarly, the condition storage 304 may be provided in an independent storage device capable of being accessed by the computer 109, instead of the storage device 111 provided in the MRI device 100.

Further, the technique of the embodiments may be applied to various imaging fields for medical use.

REFERENCE SIGNS LIST

100: MRI DEVICE
101: MAGNET
102: GRADIENT MAGNETIC FIELD COIL
103: SUBJECT
104: SEQUENCER
105: GRADIENT MAGNETIC FIELD POWER SUPPLY

106: RADIO FREQUENCY MAGNETIC FIELD GENERATOR
107: TABLE
108: RECEIVER
109: CALCULATOR
110: DISPLAY DEVICE
111: STORAGE DEVICE
112: SHIM COIL
113: SHIM POWER SUPPLY
114: TRANSMISSION COIL
115: RECEPTION COIL
117a: POWER SUPPLY POINT
117b: POWER SUPPLY POINT
117c: POWER SUPPLY POINT
117d: POWER SUPPLY POINT
200: PHANTOM
201: IMAGING REGION
202: $B_1$ DISTRIBUTION
301: REGION SETTER
302: CONDITION SETTER
303: IMAGING PARAMETER OPTIMIZER
304: CONDITION STORAGE
305: DATABASE
306: SAR DISTRIBUTION CALCULATOR
307: RF PARAMETER OPTIMIZER
308: SAR PARAMETER ADJUSTER
309: IMAGING TIME DETERMINER
310: IMAGING PARAMETER DETERMINER
311: IMAGING POSITION SETTER
312: STATIC MAGNETIC FIELD SHIMMING PART
313: RF SHIMMING PART
350: DATA
Ch1: CHANNEL
Ch2: CHANNEL
Ch3: CHANNEL
Ch4: CHANNEL

The invention claimed is:

1. A magnetic resonance imaging device comprising:
a transmission coil that includes a plurality of channels that respectively transmit radio frequency pulses to a subject;
a storage device which stores a database of data to calculate a specific absorption rate distribution for each of a plurality of predetermined subject models; and
a processor programmed to determine a plurality of imaging parameters among imaging conditions used in imaging the subject, and execute imaging using the determined imaging parameters,
wherein the processor is further programmed to:
determine the imaging parameters to optimize a radio frequency magnetic field distribution in a region of interest while suppressing a maximum value of a local specific absorption rate to be equal to or smaller than a specific absorption rate threshold value using the data in the database, and
wherein the imaging parameters includes a radio frequency magnetic field parameters which specify the radio frequency pulses to be transmitted through each of the plurality of channels and a specific absorption rate parameter which is different than the radio frequency magnetic field parameters and affects the specific absorption rate,
wherein the processor is further programmed to:
determine the radio frequency magnetic field parameters according to predetermined optimization conditions,
calculate a specific absorption rate distribution using the determined radio frequency magnetic field parameters, a latest specific absorption rate parameter, and the data in the database when the radio frequency magnetic field parameters are determined,
determine whether a maximum value of the calculated specific absorption rate distribution exceeds the specific absorption rate threshold value,
when the maximum value exceeds the specific absorption rate threshold value, adjust the specific absorption rate parameter in a predetermined range,
when the specific absorption rate parameter is changed, calculate the specific absorption rate distribution using the changed specific absorption rate parameter, determine whether a maximum value of the calculated specific absorption rate distribution using the changed specific absorption rate parameter exceeds the specific absorption rate threshold value, and
repeats, when the maximum value of the specific absorption rate distribution exceeds the specific absorption rate threshold value, a process of changing a threshold value for regulating a uniformity condition in the optimization conditions by a predetermined value, a process of determining the radio frequency magnetic field parameter again, and a process of calculating the specific absorption rate distribution using the re-determined radio frequency magnetic field parameter, until the maximum value of the specific absorption rate distribution becomes equal to or smaller than the specific absorption rate threshold value.

2. The magnetic resonance imaging device according to claim 1,
wherein the optimization conditions include the uniformity condition that a uniformity of the radio frequency magnetic field distribution is equal to or greater than a predetermined value, and a local specific absorption rate condition that the maximum value of the local specific absorption rate is equal to or smaller than the specific absorption rate threshold value, as restriction conditions.

3. The magnetic resonance imaging device according to claim 1, wherein, when the maximum value exceeds the specific absorption rate threshold value, the specific absorption rate parameter is adjusted so that the maximum value of the specific absorption rate distribution is equal to or smaller than the specific absorption rate threshold value, and
wherein the optimization conditions include the uniformity condition that the uniformity of the radio frequency magnetic field distribution is equal to or greater than a predetermined value as a restriction condition.

4. The magnetic resonance imaging device according to claim 1,
wherein the radio frequency magnetic field parameter is at least one of an amplitude and a phase of the radio frequency pulse transmitted through each of the plurality of channels of the transmission coil.

5. The magnetic resonance imaging device according to claim 3,
wherein the specific absorption rate parameter is at least one of a repetition time and the number of slices.

6. The magnetic resonance imaging device according to claim 1,
wherein the specific absorption rate parameter is at least one of a repetition time and the number of slices.

7. The magnetic resonance imaging device according to claim 1,
wherein the data in the database includes an electric field distribution of each of the plurality of channels for each of the plurality of subject models, and wherein the electric field distribution is a distribution when radio frequency magnetic field pulses having a predetermined amplitude and a phase as references are emitted once per unit time in imaging one slice.

8. The magnetic resonance imaging device according to claim 1,
wherein the processor is further programmed to:
determine the imaging parameters so that a signal value in a region where an artifact is generated is equal to or smaller than a predetermined value.

9. A magnetic resonance imaging device, comprising:
a transmission coil that includes a plurality of channels that respectively transmit radio frequency pulses to a subject;
a storage device which stores a database of data to calculate a specific absorption rate distribution for each of a plurality of predetermined subject models; and
a processor programmed to determine a plurality of imaging parameters among imaging conditions used in imaging the subject, and execute imaging using the determined imaging parameters,
wherein the processor is further programmed to:
determine the imaging parameters to optimize a radio frequency magnetic field distribution in a region of interest while suppressing a maximum value of a local specific absorption rate to be equal to or smaller than a specific absorption rate threshold value using the data in the database, and
wherein the imaging parameters includes a radio frequency magnetic field parameters which specify the radio frequency pulses to be transmitted through each of the plurality of channels and a specific absorption rate parameter which is different than the radio frequency magnetic field parameters and affects the specific absorption rate,
wherein the processor is further programmed to:
determine the radio frequency magnetic field parameters according to predetermined optimization conditions,
calculate a specific absorption rate distribution using the determined radio frequency magnetic field parameters, a latest specific absorption rate parameter, and the data in the database when the radio frequency magnetic field parameters are determined,
determine whether a maximum value of the calculated specific absorption rate distribution exceeds the specific absorption rate threshold value, and
when the maximum value exceeds the specific absorption rate threshold value, adjust the specific absorption rate parameter so that the maximum value of the specific absorption rate distribution is equal to or smaller than the specific absorption rate threshold value,
wherein the optimization conditions include a uniformity condition that the uniformity of the radio frequency magnetic field distribution is equal to or greater than a predetermined value as a restriction condition, and
wherein the processor is further programmed to:
calculate a time relating to imaging using the adjusted specific absorption rate parameter,
determine whether the calculated imaging time is within an allowable range, and
when the calculated imaging time is not within the allowable range, determine a threshold value for regulating the uniformity condition in the optimization conditions by a predetermined value, and determine the radio frequency magnetic field parameter again.

10. The magnetic resonance imaging device according to claim 9,
wherein the radio frequency magnetic field parameter is at least one of an amplitude and a phase of the radio frequency pulse transmitted through each of the plurality of channels of the transmission coil.

11. The magnetic resonance imaging device according to claim 9,
wherein the specific absorption rate parameter is at least one of a repetition time and the number of slices.

12. The magnetic resonance imaging device according to claim 9,
wherein the data in the database includes an electric field distribution of each of the plurality of channels for each of the plurality of subject models, and
wherein the electric field distribution is a distribution when radio frequency magnetic field pulses having a predetermined amplitude and a phase as references are emitted once per unit time in imaging one slice.

13. The magnetic resonance imaging device according to claim 9,
wherein the processor is further programmed to:
determine the imaging parameters so that a signal value in a region where an artifact is generated is equal to or smaller than a predetermined value.

* * * * *